United States Patent
Murabayashi et al.

(10) Patent No.: US 10,918,418 B2
(45) Date of Patent: Feb. 16, 2021

(54) SPINAL IMPLANT

(71) Applicant: KYOCERA Corporation, Kyoto (JP)

(72) Inventors: Hajime Murabayashi, Kyoto (JP); Yusuke Majima, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/753,776

(22) PCT Filed: Aug. 19, 2016

(86) PCT No.: PCT/JP2016/074260
§ 371 (c)(1),
(2) Date: Feb. 20, 2018

(87) PCT Pub. No.: WO2017/033866
PCT Pub. Date: Mar. 2, 2017

(65) Prior Publication Data
US 2018/0243010 A1   Aug. 30, 2018

(30) Foreign Application Priority Data

Aug. 21, 2015  (JP) .................................. 2015-163911
Aug. 19, 2016  (JP) .................................. 2016-161110

(51) Int. Cl.
*A61B 17/70*    (2006.01)
*A61B 17/86*    (2006.01)
*A61B 17/00*    (2006.01)

(52) U.S. Cl.
CPC .......... *A61B 17/7032* (2013.01); *A61B 17/70* (2013.01); *A61B 17/7037* (2013.01); *A61B 17/8605* (2013.01); *A61B 2017/00862* (2013.01)

(58) Field of Classification Search
CPC ........................ A61B 17/7032; A61B 17/7085
(Continued)

(56) References Cited

U.S. PATENT DOCUMENTS 5,672,176 A * 9/1997 Biedermann ...... A61B 17/7037
606/271
8,409,256 B2   4/2013 Arnold et al.
(Continued)

FOREIGN PATENT DOCUMENTS

JP    2013-500127 A    1/2013
JP    2013-094675 A    5/2013
(Continued)

OTHER PUBLICATIONS

International Search Report, PCT/JP2016/074260, dated Oct. 23, 2016, 2 pgs.

*Primary Examiner* — Ellen C Hammond
*Assistant Examiner* — Tara Rose E Carter
(74) *Attorney, Agent, or Firm* — Volpe Koenig

(57) ABSTRACT

Provided is a spinal implant which includes a compact housing usable in common regardless of a bone screw diameter and is good at assembling properties. A spinal implant includes a screw head holding member, a housing, and an insert. The screw head holding member includes a cylindrical section which is elastically deformable in the radial direction and which includes a support section that supports a screw head from a lower side. The housing accommodates the screw head holding member holding the screw head. The screw head holding member further includes an elastic deformable section which is elastically deformable in the radial direction of the cylindrical section so that an engagement section can engage with the inner circumferential surface of the housing.

10 Claims, 24 Drawing Sheets

(58) Field of Classification Search
USPC .................................................. 606/268, 269
See application file for complete search history.

(56) References Cited

U.S. PATENT DOCUMENTS

| | | |
|---|---|---|
| 9,339,304 B2 | 5/2016 | Biedermann et al. |
| 9,492,204 B2 | 11/2016 | Biedermann et al. |
| 9,629,662 B2 | 4/2017 | Arnold et al. |
| 2008/0161853 A1 | 7/2008 | Arnold et al. |
| 2008/0161863 A1 | 7/2008 | Arnold et al. |
| 2010/0152787 A1* | 6/2010 | Walsh ................ A61B 17/7037 606/308 |
| 2011/0098755 A1 | 4/2011 | Jackson et al. |
| 2012/0035670 A1* | 2/2012 | Jackson ............. A61B 17/7032 606/305 |
| 2012/0179212 A1 | 7/2012 | Jackson et al. |
| 2013/0110178 A1 | 5/2013 | Biedermann et al. |
| 2013/0123858 A1 | 5/2013 | Attia |
| 2013/0197583 A1 | 8/2013 | Arnold et al. |
| 2015/0088207 A1 | 3/2015 | Arnold et al. |
| 2015/0142059 A1 | 5/2015 | Biedermann et al. |

FOREIGN PATENT DOCUMENTS

| | | |
|---|---|---|
| JP | 5437074 B2 | 3/2014 |
| JP | 2014-516263 A | 7/2014 |
| JP | 2015-093200 A | 5/2015 |
| WO | 2008/085347 A1 | 7/2008 |
| WO | 2008/085369 A1 | 7/2008 |
| WO | 2011/043805 A1 | 4/2011 |
| WO | 2011/131849 A1 | 10/2011 |

* cited by examiner

FIG. 6
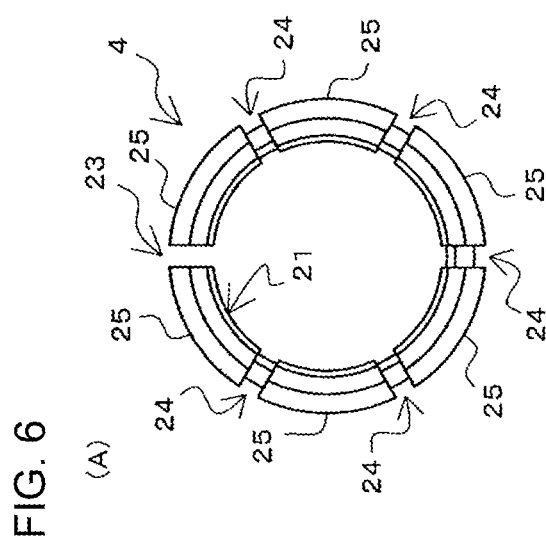
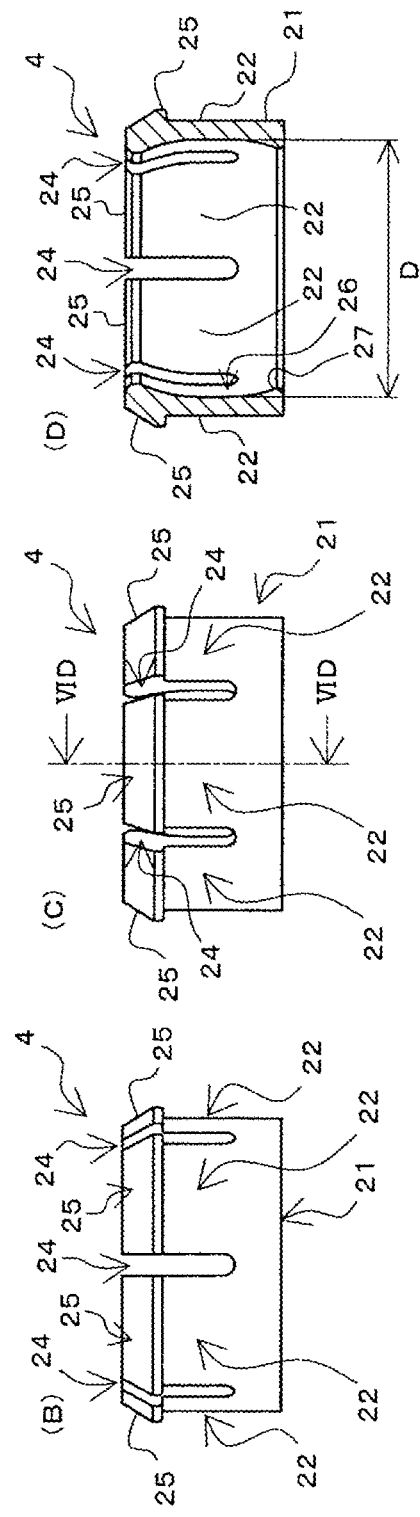

FIG. 12
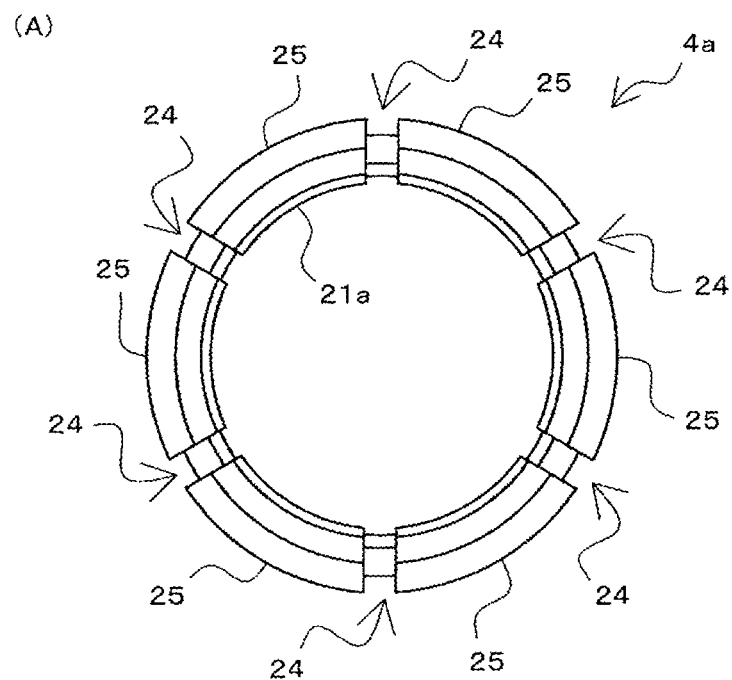
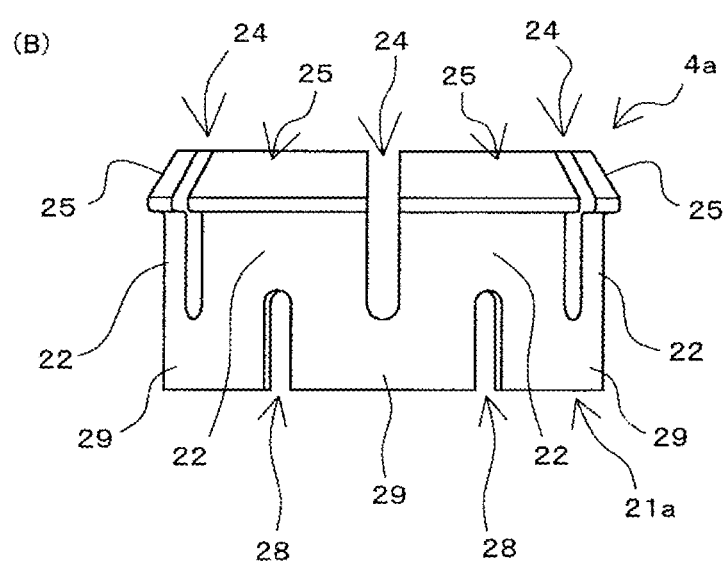

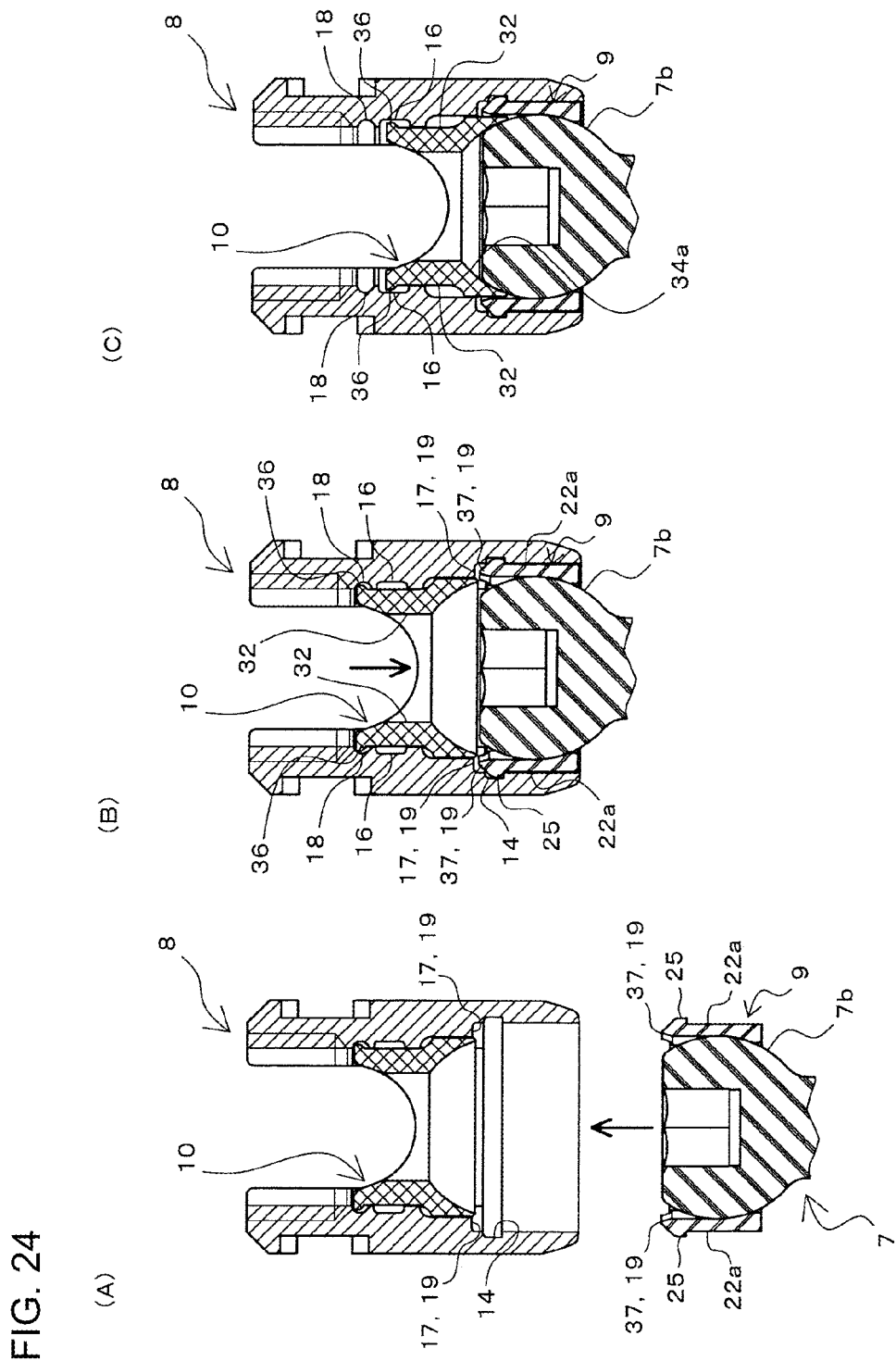

SPINAL IMPLANT

TECHNICAL FIELD

The present invention relates to a spinal implant to hold a fixing rod that fixes vertebrae to each other.

BACKGROUND ART

Heretofore, a spinal implant to hold a fixing rod that fixes vertebrae to each other has been known. As such a spinal implant, for example, PTL 1 discloses a bone anchor (spinal implant) including a receiver member (housing) and a bone engagement member (screw) inserted into the housing from above.

CITATION LIST

Patent Literature

PTL 1: Japanese Patent No. 5437074

SUMMARY OF INVENTION

Technical Problem

With the configuration in which the screw is inserted into the housing from above as described in PTL 1, the housing needs to have a size corresponding to the screw diameter and the housing is not in common use. In order to use the housing in common, it is necessary to increase the size of the housing.

The present invention is to solve the aforementioned problem, and an object thereof is to provide a spinal implant which includes a compact housing usable in common regardless of the bone screw size and which is good at assembling properties.

Solution to Problem (1) A spinal implant according to an aspect of the present invention to achieve the aforementioned object is a spinal implant that fixes a rod to a vertebra and includes: a screw head holding member including a cylindrical section which is elastically deformable in a radial direction and which has a cylindrical shape and holds a screw head of a bone screw from outside, the bone screw being fixed to the vertebra with a screw body screwed to the vertebra, the screw body including an external thread on an outer circumference of the screw body, the cylindrical section including a support section that supports the screw head from a lower side where the lower side denotes a side to which the screw body extends from the screw head; a housing which accommodates the screw head holding member holding the screw head and in which an inner circumferential surface of the housing engages with an engagement section in the screw head holding member; and an insert which is disposed on top of the screw head within the housing and which fixes the housing to the screw head by pressing the screw head downward while receiving pressing force by the rod pressed by a set screw screwed to the housing. The screw head holding member further includes an elastic deformable section which is elastically deformable in a radial direction of the cylindrical section and which allows the engagement section to engage with the inner circumferential surface of the housing.

In this configuration, the screw head holding member, housing, and insert exert forces on each other to fix the rod to the bone screw fixed to each vertebra of a patient. The vertebrae of the patient are thereby fixed to each other.

Specifically, in this configuration, the screw head holding member holding the screw head is accommodated within the housing and engages with the housing. In this configuration, moreover, the insert disposed in the housing is subjected to pressing force by the rod fixed to the housing by the set screw screwed to the housing and presses the screw head downward, so that the housing is fixed to the screw head. Accordingly, the position and orientation of the rod with respect to the bone screw can be fixed. The rod is fixed as described above, where the rod is laid across all of the bone screws fixed to vertebrae, of a patient, to be fixed. The vertebrae of the patient can be thereby fixed to each other.

In this configuration, the support section in the cylindrical section of the screw head holding member supports the screw head from the lower side. The screw head is thus prevented by the screw head holding member from separating from the housing. Additionally, in this configuration, the cylindrical section, which includes the support section, is configured to increase in diameter. At the assembly of the spinal implant, therefore, the screw head is accommodated within the cylindrical section by inserting the screw head into the screw head holding member from below the screw head holding member.

If a spinal implant is assembled by inserting a bone screw into a screw head holder (or a housing) from above, for example, it is necessary to determine the size of the housing depending on the screw diameter of the bone screw, and the housing cannot be used in common. In order to use the housing in common, the housing size needs to be increased.

On the other hand, with the aforementioned configuration, the cylindrical section is elastically deformable (capable of increasing or decreasing in diameter) in the radial direction. This allows for the assembly process in which the screw head can be inserted into the screw head holding member from below and the screw head holding member holding the screw head is inserted into the housing from below the housing. The housing reduced in size can be used in common regardless of the size of the screw diameter.

With this configuration, the section having the function to hold the screw head in the housing and the section having the function to prevent the screw head from separating from the housing are composed of one member (the screw head holding member). This can reduce the number of components compared with when the sections having the aforementioned functions are composed of different components, for example. It is therefore possible to provide the spinal implant good at assembling properties.

By disposing the elastic deformable section which can elastically deform within the housing to the screw head holding member like this configuration, the screw head holding member is smoothly inserted into the housing and easily engages with the housing, when the screw head holding member holding the screw head is accommodated within the housing in the assembly of the spinal implant. It is therefore possible to provide the spinal implant good at assembling properties.

With this configuration, it is possible to provide the spinal implant in which the compact housing is used in common regardless of the size of the bone screw and which is good at assembling properties.

(2) Preferably, the cylindrical section is divided in the circumferential direction by a notch extending in a top-bottom direction and is C-shaped when viewed in the top-bottom direction.

With this configuration, the cylindrical section includes the notch. Accordingly, the cylindrical section capable of increasing and decreasing in diameter can be formed easily.

(3) Preferably, the cylindrical section includes a slit extending from a lower end of the cylindrical section to a position below an upper end of the cylindrical section.

In this configuration, a plurality of slits is formed in the cylindrical section. The cylindrical section is therefore capable of increasing and decreasing in diameter. With the configuration, the screw head holding member can take a wide variety of shapes.

(4) Preferably, the spinal implant further includes a housing rotation restricting mechanism that limits rotation of the housing relative to the screw head holding member.

With this configuration, rotation of the housing relative to the screw head holding member is limited. This can prevent the housing from rotating and changing the orientation under the own weight or by any external force after the bone screw is embedded in the patient's bone and the housing is set to a predetermined orientation with respect to the bone screw during the time of surgery. With this configuration, the spinal implant can be held at a predetermined orientation after being fixed to a bone, providing good handling properties.

(5) Preferably, the housing rotation restricting mechanism includes: a protrusion protruding upward from the elastic deformable section; and a recess depressed upward in an inner side of the housing and covering at least a top portion of the protrusion from above.

With this configuration, the housing rotation restricting mechanism includes the protrusion and recess, which are elements having comparatively simplified shapes. According to this configuration, the housing rotation restricting mechanism is implemented in a simple form.

(6) Preferably, the screw head holding member further includes a plurality of segmented sections each of which extends from the cylindrical section in an axial direction of the cylindrical section and includes the engagement section at a top portion of each of the segmented sections. The plurality of segmented sections serves as the elastic deformable section.

In this configuration, the plurality of segmented sections constitutes the elastic deformable section. The configuration of the elastic deformable section is thus simplified.

(7) Preferably, the plurality of segmented sections extends upward from the cylindrical section.

In this configuration, the plurality of segmented sections is disposed above the cylindrical section. By disposing the segmented sections in the portion above the cylindrical section which is less limited in terms of space in the housing than the other portion, the space in the housing is utilized effectively. This allows the housing to have a reduced size.

(8) Preferably, the engagement section includes a pawl section protruding outward from the top portion of the corresponding segmented section, and the housing includes a groove that engages with the pawl section.

In this configuration, the pawl sections protrude as the engagement section outward from the top portions of the segmented sections while the groove configured to engage with the pawl sections is disposed in the housing. This can simplify the shape of the engagement section.

(9) Preferably, an outer circumferential surface of the insert is located inside of a portion, where the pawl section is disposed, of the segmented section.

In this configuration, even if the pawl sections are subjected to any radially inward force due to any cause and likely to bend inward, the pawl sections are prevented from bending, by the outer circumferential surface of the insert. This can prevent the pawl sections from being disengaged from the groove of the housing.

(10) Preferably, a lower section of the insert serves as a lower base having an outer diameter greater than an outer diameter of an upper base which is a section of the insert above the lower base, and an outer circumferential surface of the lower base is located inside of the portion, where the pawl section is disposed, of the segmented section.

With this configuration, the lower base of the insert can be comparatively large. The area of contact between the insert and screw head can be accordingly large. When the rod is fixed by the set screw screwed to the housing, the insert comes into tight contact with the screw head through a wider area, so that the force to fix the housing to the bone screw is increased.

(11) Preferably, an inner space surrounded by the portions of the plurality of segmented sections where the pawl sections are disposed has a cylindrical shape extending in the top-bottom direction.

If the inner space surrounded by the portions of the segmented sections where the pawl sections are disposed narrows inward with the height, for example, the lower base of the insert disposed within the same area is limited in size.

In this respect, in the above configuration, the inner space surrounded by the portions of the segmented sections where the pawl sections are disposed does not narrow inward and forms a cylindrical shape extending in the top-bottom direction. Even if the outer diameter of the lower base of the insert is increased, therefore, the lower base does not interfere with the screw head holding member. With this configuration, the head screw holding member is suitable for the insert in which the lower base has a larger diameter.

(12) Preferably, the inner circumferential surface of the housing surrounds an outer circumferential surface of the cylindrical section.

In this configuration, if the screw head is likely to separate from the cylindrical section downward, the outer circumferential surface of the cylindrical section is covered with the inner circumferential surface of the housing, and the cylindrical section does not greatly increase in diameter. This can prevent the screw head from separating from the housing.

(13) Preferably, an inner circumferential surface of the cylindrical section includes: a lower concave curve surface that is disposed as a lower section of the inner circumferential surface and supports a lower portion of the screw head; and a cylindrical inner surface extending upward from the lower concave curve surface.

With this configuration, in the state where the lower portion of the screw head is supported by the lower concave curve surface, space is formed between the plurality of segmented sections and screw head. This ensures enough space for the segmented sections to elastically deform, on the back (the screw head side) of the plurality of segmented sections as the elastic deformable section. With this configuration, when the screw head holding member holding the screw head is inserted into the housing from below, the plurality of segmented sections elastically deforms, allowing the screw head holding member to engage with the housing from below.

(14) Preferably, the inner diameter of the cylindrical inner surface is smaller than the outer diameter of the screw head.

In this configuration, when the screw head is accommodated within the cylindrical section, the screw head is tightened inward by the cylindrical inner surface. With this configuration, the screw head is therefore easily retained within the cylindrical section.

(15) Preferably, the insert includes an insert engagement section that engages with the inner circumferential surface of the housing, and the insert engagement section engages with the inner circumferential surface of the housing and limits circumferential movement of the insert relative to the housing.

In this configuration, the position of the insert in the housing is easily fixed.

(16) Preferably, the inner circumferential surface of the housing includes a housing-engaged section in a shape of a recess with which the insert engagement section having a protruding shape engages, and a portion of the inner circumferential surface of the housing above the housing-engaged section includes an arc-shaped rotation allowing groove that allows rotation of the insert engagement section in the housing.

With this configuration, in the spinal implant including the assembly process of inserting the insert into the housing from below, the assembling work of the insert to the housing is facilitated. Specifically, when the insert is inserted into the housing from below, the insert engagement section is inserted to the same height as the rotation allowing groove, then rotated to the position above the housing-engaged section, and then pressed downward to engage with the housing-engaged section. With this configuration, it is possible to provide the spinal implant good at assembling properties.

With this configuration, the insert and the screw head holding member that is holding the screw head can be inserted into the housing from below the housing. With this configuration, all the components within the housing can be inserted from the same direction. It is therefore possible to provide the spinal implant good at assembling properties.

(17) Preferably, the spinal implant further includes the bone screw.

With this configuration, it is possible to provide the spinal implant which includes the compact housing usable in common regardless of the size of the screw diameter, is good at assembling properties, and further includes a bone screw.

Advantageous Effects of Invention

According to the present invention, it is possible to provide a spinal implant which includes a compact housing usable in common regardless of the size of the bone screw and is good at assembling properties.

BRIEF DESCRIPTION OF DRAWINGS

FIGS. 6(A) to 6(D) illustrate the shape of a washer, FIGS. 6(A) to 6(D) being a plan view, a front view, a side view, and a sectional view along a line VID-VID of FIG. 6(C), respectively.

FIGS. 12(A) and 12(B) illustrate the shape of a washer of a spinal implant according to a modification, FIGS. 12(A) and 12(B) being a plan view and a front view, respectively.

FIG. 23(B) illustrating the state of the insert inserted in the housing; and FIG. 23(C) illustrating the state of the insert rotated in the housing.

FIGS. 24(A) to 24(C) illustrate processes performed in steps S8 and S9 in FIG. 21, FIG. 24(A) illustrating the state of the screw head and washer before the screw head and washer are inserted into the housing; FIG. 24(B) illustrating the state of the screw head and washer inserted in the housing; and FIG. 24(C) illustrating the state where projections of the insert are engaged with recesses of the housing.

DESCRIPTION OF EMBODIMENTS

Hereinafter, an embodiment of the present invention is described with reference to the drawings. The present invention is applicable to a wide variety of spinal implants to hold a fixing rod that fixes vertebrae to each other.

Figure 1:
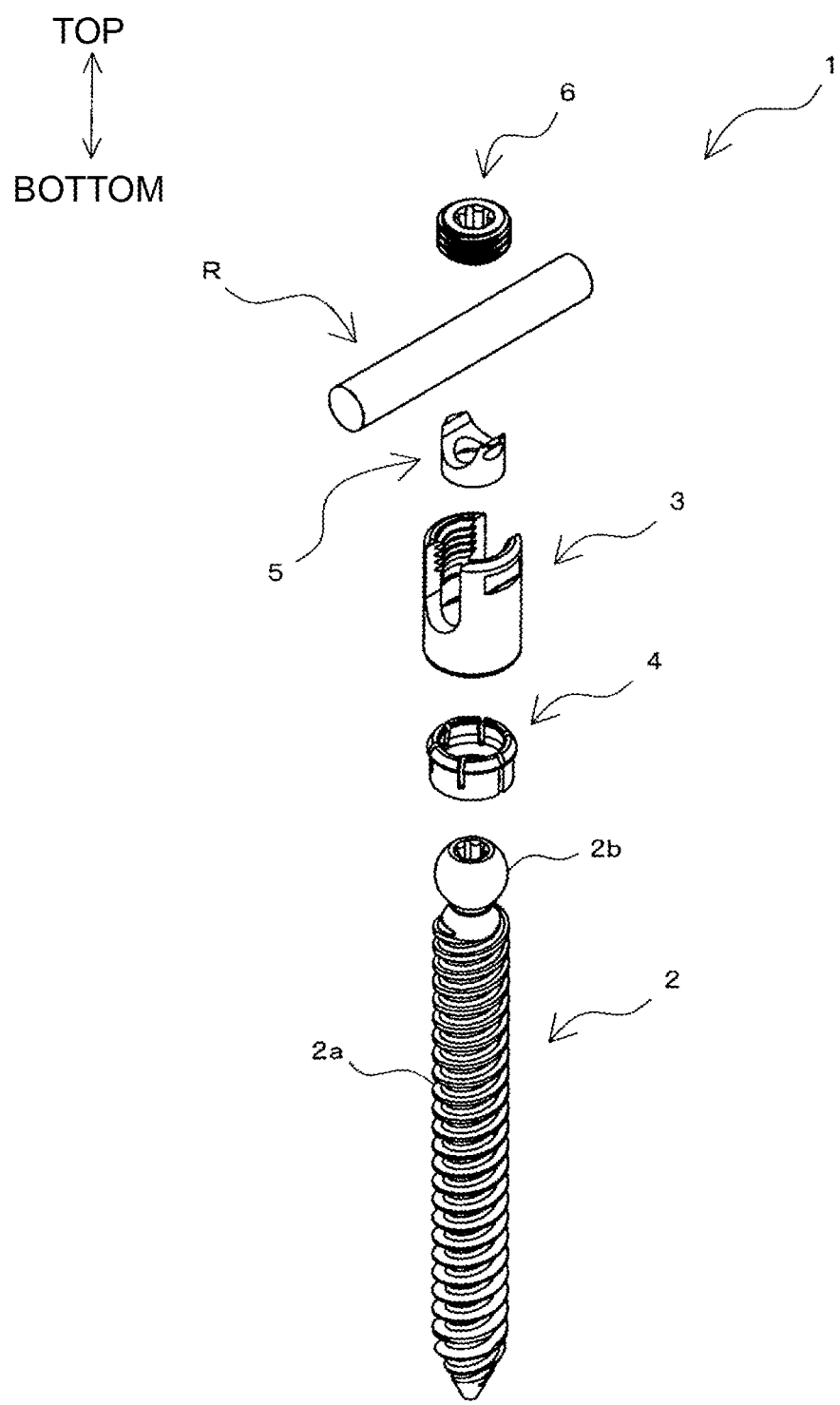
FIG. 1 is an exploded perspective view illustrating a spinal implant according to an embodiment together with a fixing rod fixed to a vertebra by using the spinal implant.
Figure 2:
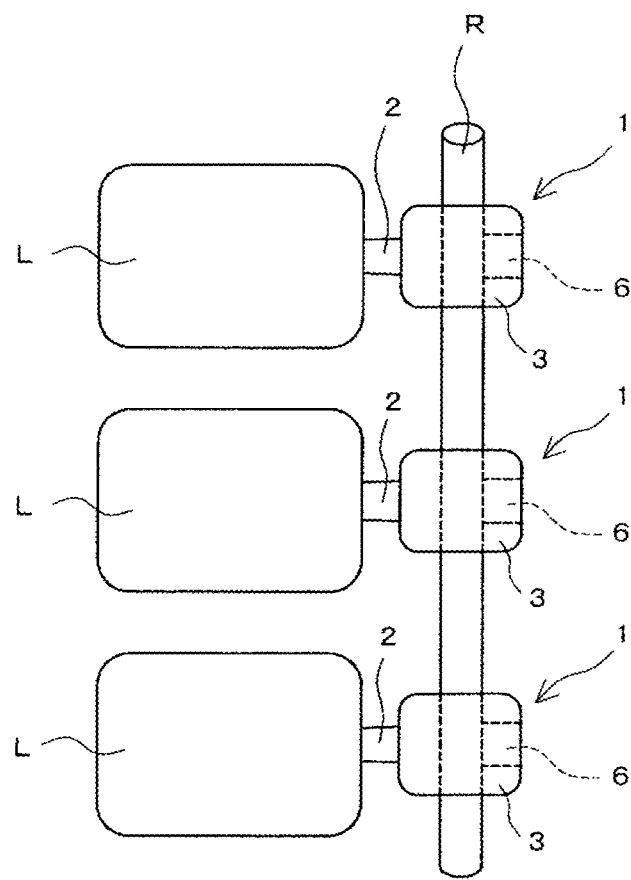
FIG. 2 schematically illustrates usage of the spinal implant illustrated in FIG. 1.
Figure 3:
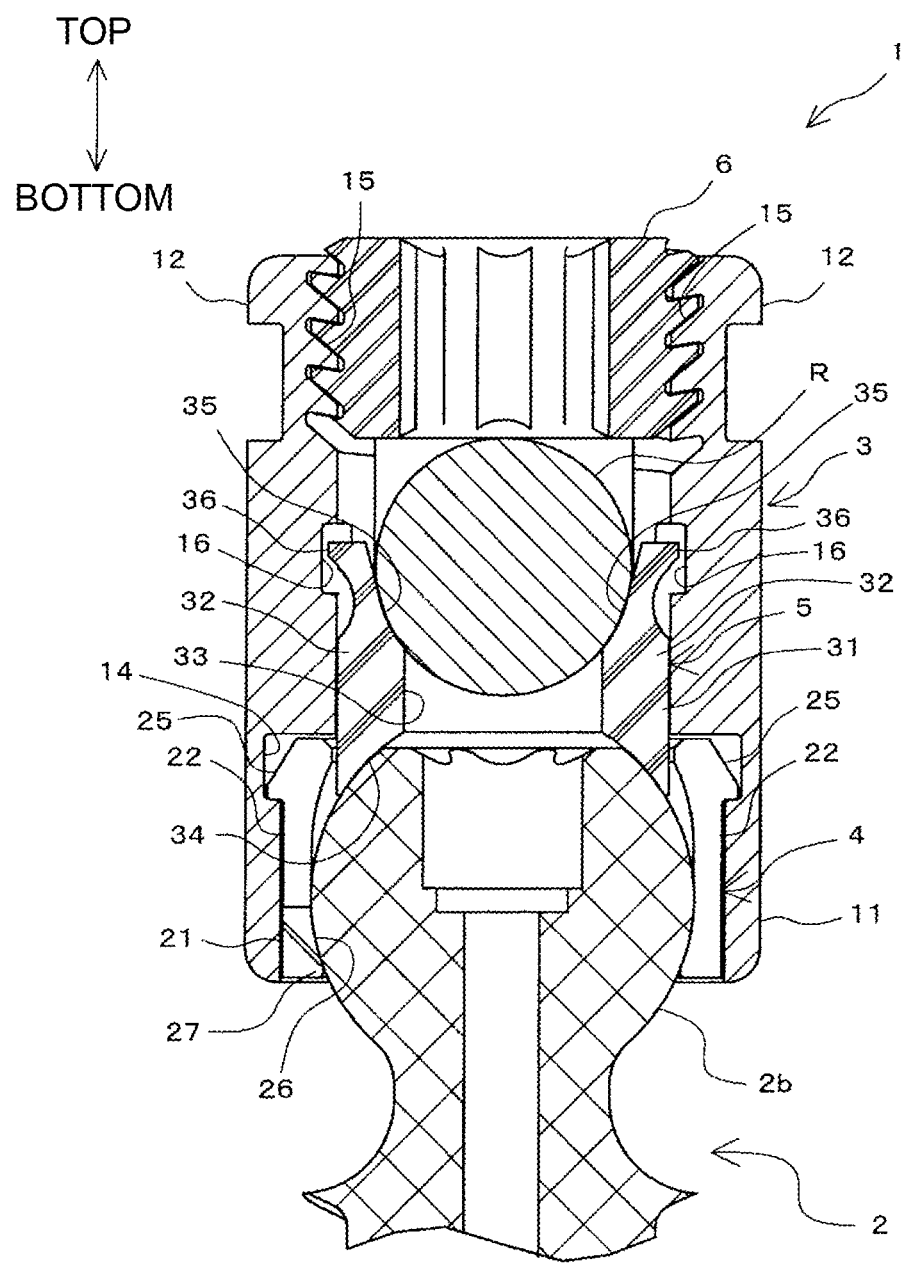
FIG. 3 is a partial longitudinal sectional view of the spinal implant.
Figure 4:
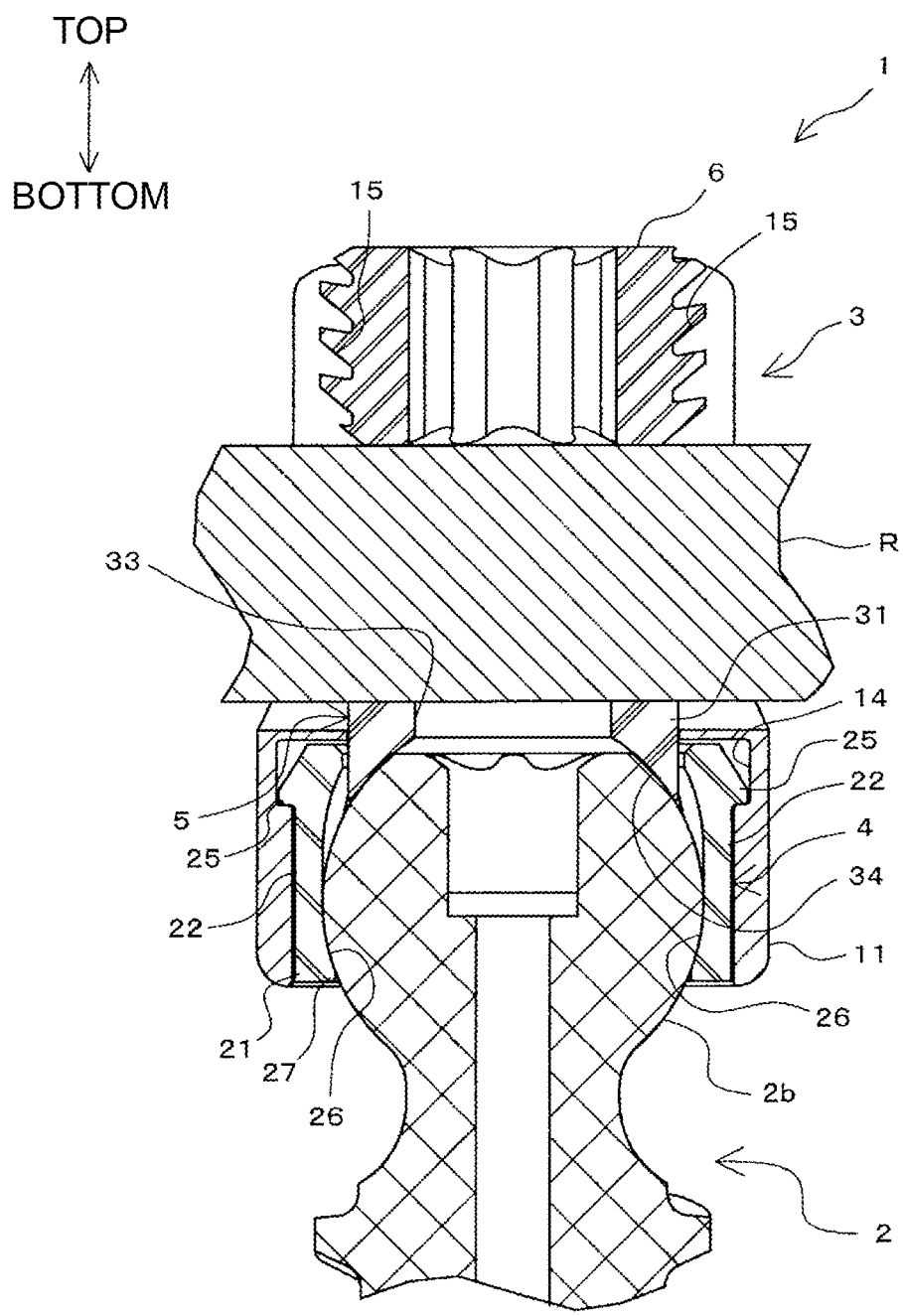
FIG. 4 is a partial longitudinal sectional view of the spinal implant at a different position from that of FIG. 3.

FIG. 1 is an exploded perspective view illustrating a spinal implant according to the embodiment together with a fixing rod R which is fixed to a vertebra L with the spinal implant 1. FIG. 2 schematically illustrates usage of the spinal implant 1 in FIG. 1. FIG. 3 is a partial longitudinal sectional view of the spinal implant 1. FIG. 4 is a partial longitudinal sectional view of the spinal implant 1 at a different position from that of FIG. 3.

The spinal implant 1 is a device used in spinal fusion. As illustrated in FIG. 1, the spinal implant 1 includes a screw 2, a housing 3, a washer 4 (a screw head holding member), an insert 5, and a set screw 6. The screw 2, housing 3, washer 4, insert 5, and set screw 6 are combined and exert forces on each other in the spinal implant 1 to fix the fixing rod R to the spinal implant 1.

With reference to FIG. 2, the spinal implant 1 is fixed to each of adjacent vertebrae L such that the screw 2 of the spinal implant 1 is screwed to the vertebra L. The fixing rod R is laid across all of the spinal implants 1 fixed to the respective vertebrae L as illustrated in FIG. 2. In this state, the set screw 6 is fixed to the housing 3. The vertebrae L restored to normal positions and normal states are therefore fixed to each other. This can maintain the patient's lumber vertebrae in a predetermined state and reduce strain on the back.

[Configuration of Elements of Spinal Implant]

With reference to FIG. 1, the screw 2 includes a screw body 2a and a screw head 2b, which are integrally formed. The screw body 2a is a thread section with an external thread in the outer circumference. The screw head 2b is a substantially spherical section and is integrally disposed in the side (the proximal end) opposite to the tip (a part embedded in a vertebra L) of the screw body 2a.

Figure 5:
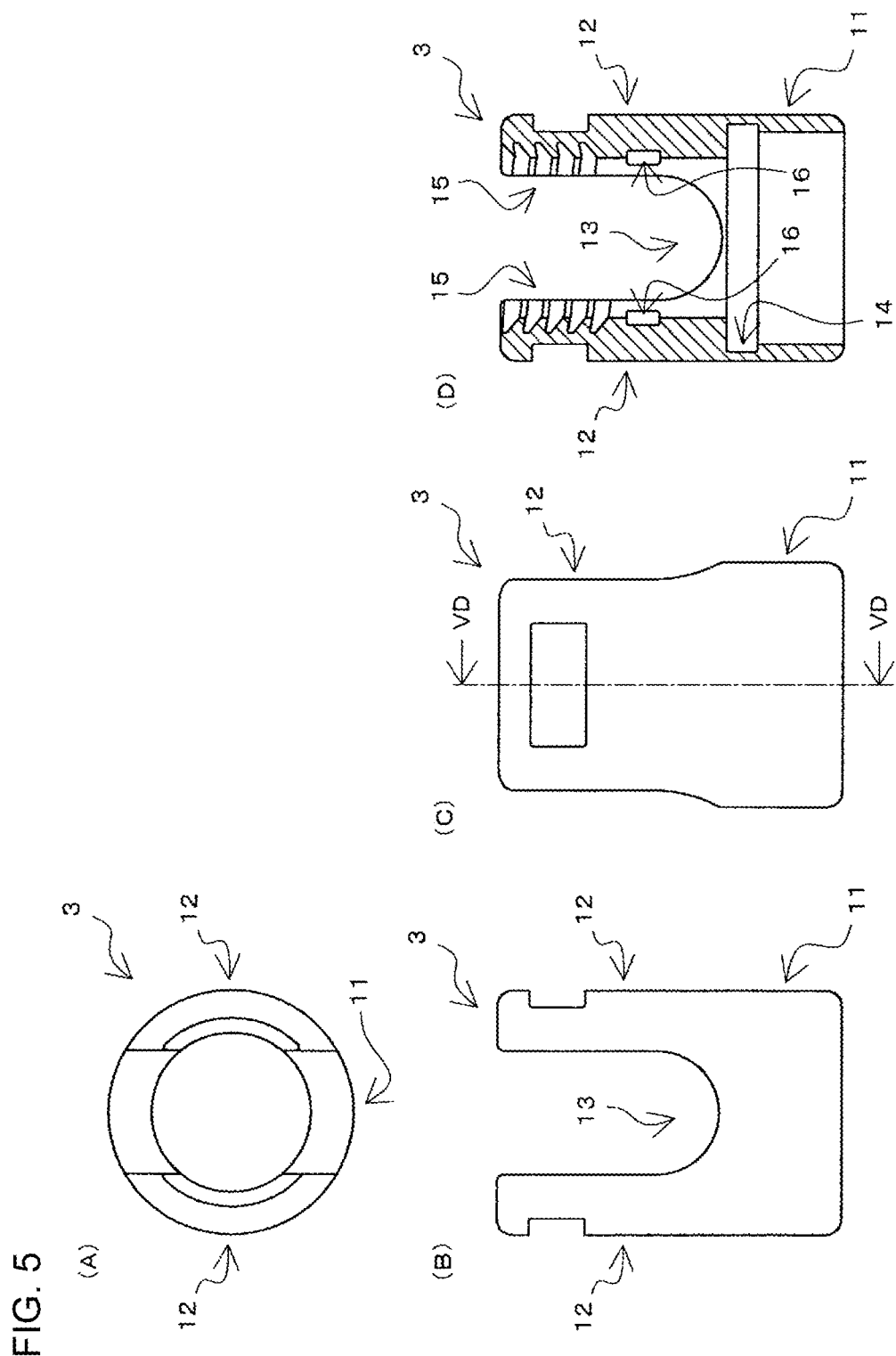
FIGS. 5(A) to 5(D) illustrate the shape of a housing, FIGS. 5(A) to 5(D) being a plan view, a front view, a side view, and a sectional view along a line VD-VD of FIG. 5C, respectively.

FIG. 5 illustrates the shape of the housing 3. FIGS. 5(A) to 5(D) are a plan view, a front view, a side view, and a sectional view taken along a line VD-VD in FIG. 5C, respectively. The housing 3 is attached so as to be rotatable relative to the screw head 2b. The housing 3 includes a base 11 having a substantially cylindrical shape and a pair of tabs 12 extending upward from the base 11 with reference to FIGS. 1 and 5(A) to 5(D). The base 11 and tabs 12 are integrally formed. Between the pair of tabs 12, a pair of slits 13 is formed. In the pair of slits 13, the fixing rod R is disposed.

The base 11 includes an annular groove 14 extending in an annular form in the portion of the inner circumferential surface of the base 11 on the tabs 12 side. The annular groove 14 engages with pawl sections 25 of the washer 4 described later in detail.

In an upper part of the inner side surface of each tab 12, an internal thread 15 helically extends in the top-bottom direction. The internal threads 15 are screwed to the set screw 6.

In the portion of the inner circumferential surface of each tab 12 slightly below the corresponding internal thread 15, a recess 16 is formed. The recesses 16 engage with protrusions of the insert 5, described later in detail.

FIG. 6 illustrates the shape of the washer 4. FIGS. 6(A) to 6(D) are a plan view, a front view, a side view, and a sectional view taken along a line VID-VID in FIG. 6(C), respectively.

The washer 4 is a member to prevent the screw head 2b from separating from the housing 3. The washer 4 engages with the inner circumferential surface of the housing 3 within the housing 3. The washer 4 includes a cylindrical section 21 and a plurality of segmented sections 22, which are integrally formed.

In other words, the washer 4 is composed of one member in this embodiment.

The cylindrical section 21 constitutes the lower half of the washer 4 and is a substantially cylindrical portion opened in the top-bottom direction. The cylindrical section 21 includes a notch 23, which extends in the top-bottom direction in a part of the peripheral wall of the cylindrical section 21. The cylindrical section 21 is circumferentially divided by the notch 23 and has a C shape when viewed in the top-bottom direction. A maximum inner diameter D (see FIG. 6(D)), which is the largest inner diameter of the cylindrical section 21, is a little smaller than the outer diameter of the screw head 2b.

The segmented sections 22 extend upward from the upper end of the cylindrical section 21. The segmented sections 22 are formed with space therebetween in the circumferential direction. Between adjacent ones of the segmented sections 22, slits 24 are formed. The slits 24 extend from the upper end of the washer 4 to the middle of the washer 4 in the top-bottom direction. Each segmented section 22 is disposed as an elastic deformable section that elastically deforms when the washer 4 holding the screw head 2b is inserted into the housing 3 (described later in detail).

The segmented sections 22 include the respective pawl sections 25. Each pawl section 25 protrudes outward from a top portion of the corresponding segmented section 22. Each pawl section 25 is an engagement section configured to engage with the annular groove 14 of the housing 3.

The washer 4 further includes a support section 27.

The support section 27 is a section in the lower end of the inner circumference of the cylindrical section 21 and protrudes toward the inside of the cylindrical section 21. When the screw head 2b is held within the washer 4, the support section 27 supports the screw head 2b from the lower side to prevent the washer 4 from being detached from the screw head 2b.

Figure 7:
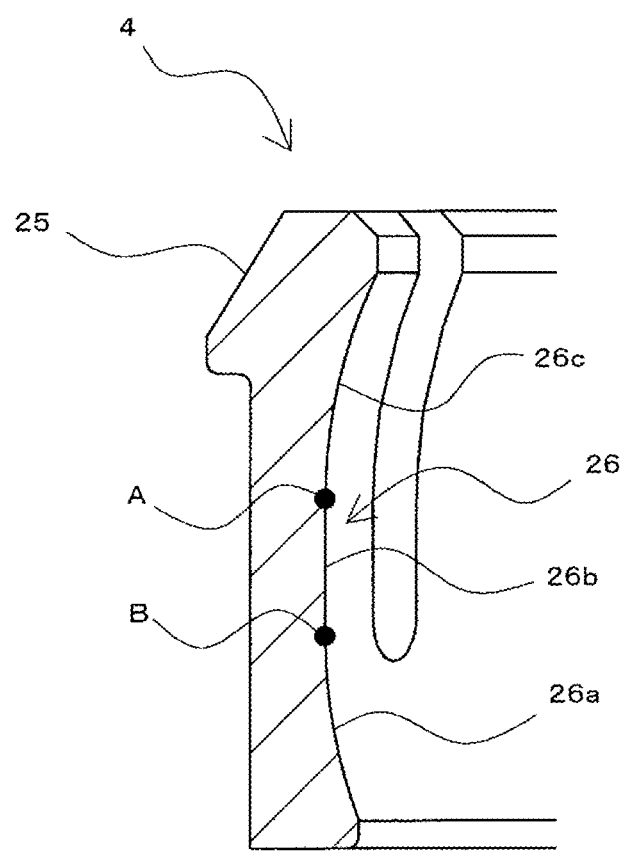
FIG. 7 is a partial enlarged view of FIG. 6(D) and illustrates the profile of the inner surface of the washer.

FIG. 7 is a partial enlarged view of FIG. 6(D). FIG. 7 is an illustration for describing the shape of the inner circumferential surface 26 of the washer 4. The inner circumferential surface 26 of the washer 4 includes a lower concave curve surface 26a, a cylindrical inner surface 26b, and an upper concave surface 26c.

The lower concave curve surface 26a is a part of a spherical concave surface. The lower concave curve surface 26a is disposed as a lower section of the inner circumferential surface 26 of the washer 4. The lower concave curve surface 26a supports the lower portion of the screw head 2b. The curvature radius of the lower concave curve surface 26a is smaller than the curvature radius of the screw head.

The cylindrical inner surface 26b is located above the lower concave curve surface 26a in the inner circumferential surface 26 of the washer 4. The cylindrical inner surface 26b extends upward from the upper end of the lower concave curve surface 26a. When viewed in a direction perpendicular to the top-bottom direction, the cylindrical inner surface 26b has a straight line profile extending in the top-bottom direction. Specifically, with reference to FIG. 7, the cylindrical inner surface 26b extends linearly in the top-bottom direction between an upper end B of the lower concave curve surface 26a and a lower end A of the upper concave surface 26c, which is described later in detail. The cylindrical inner surface 26b is a maximum inner diameter section having the largest inner diameter in the inner circumferential surface 26 of the washer 4. The radius of the cylindrical inner surface 26b is the same as the curvature radius of the lower concave curve surface 26a. The inner diameter of the cylindrical inner surface 26b is therefore smaller than the outer diameter of the screw head 2b.

The upper concave surface 26c is a part of a spherical concave surface. The upper concave surface 26c is an upper section of the inner circumferential surface 26 of the washer 4. The aforementioned pawl sections 25 are formed outside of the upper concave surface 26c. The curvature radius of the upper concave surface 26c is the same as that of the lower concave curve surface 26a and is smaller than the radius of the screw head 2b.

Figure 8:
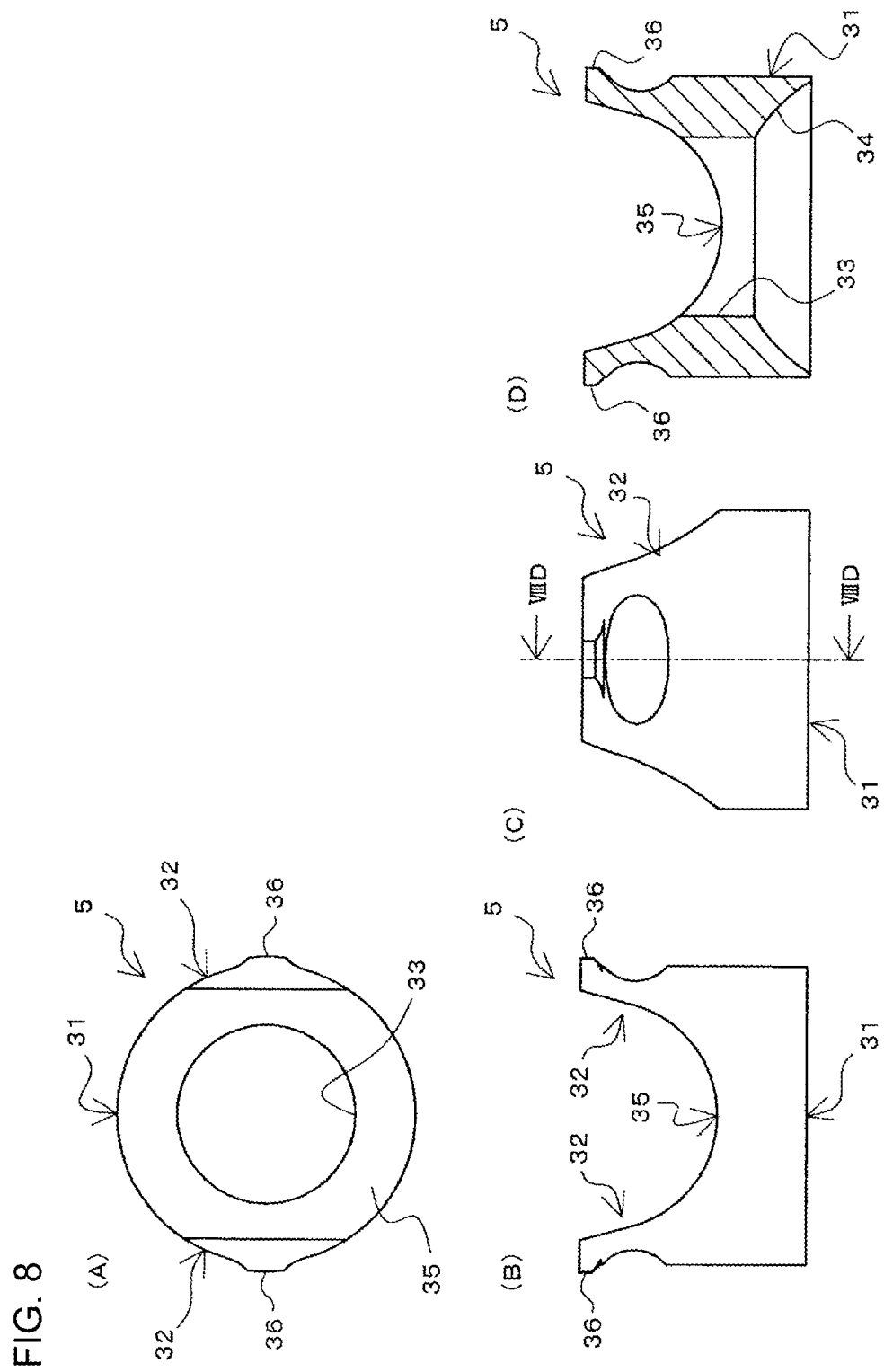
FIGS. 8(A) to 8(D) illustrate the shape of an insert, FIGS. 8(A) to 8(D) being a plan view, a front view, a side view, and a sectional view along a line VIIID-VIIID of FIG. 8(C), respectively.

FIG. 8 illustrates the shape of the insert 5. FIGS. 8(A) to 8(D) are a plan view, a front view, a side view, and a sectional view taken along a line VIIID-VIIID in FIG. 8(C), respectively. The insert 5 is a member accommodated in the housing 3. The insert 5 is pressed from above by the fixing rod R and thereby presses the top of the screw head 2b downward. The insert 5 includes a cylindrical base 31 and a pair of walls 32, which are integrally formed. The pair of walls 32 extends upward from the base 31.

The base 31 includes a through-hole 33 penetrating in the top-bottom direction. In the lower portion of the base 31, a lower curved section 34 is formed. The lower curved section 34 has a curved shape that allows the upper part of the screw head 2b to fit into the lower curved section 34. In the top of the base 31, an upper curved section 35 is formed. The upper curved section 35 has a curved shape that allows lower part of the fixing rod R to fit into the upper curved section 35.

The paired walls 32 face each other. The fixing rod R is interposed and held between the pair of walls 32. In the outside of the upper end of each wall 32, a protrusion 36 protrudes outward from the upper end of the wall 32. These protrusions 36 are disposed as insert engagement sections configured to engage with the respective recesses 16 of the housing 3.

With reference to FIG. 1, the set screw 6 is disposed as a screw which includes an external thread on the outer circumference and is thin in the top-bottom direction. The set screw 6 is screwed to the internal threads 15, which are formed in the housing 3.

[Assembly Process of Spinal Implant]

Figure 9:
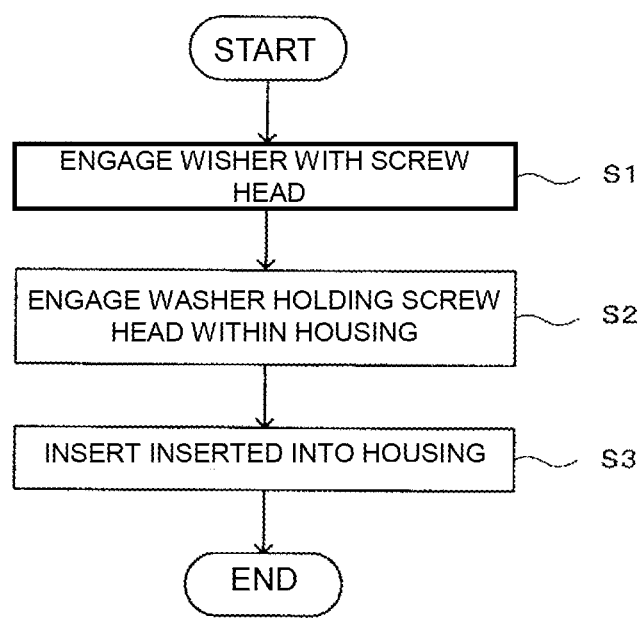
FIG. 9 is a flowchart illustrating an assembly process of the spinal implant.

FIG. 9 is a flowchart illustrating the assembly process of the spinal implant 1. Hereinafter, the assembly process of the spinal implant 1 is described with reference to FIG. 9 and the like.

First, in step S1, the washer 4 is engaged with the screw head 2b. Specifically, the screw head 2b is inserted upward into the washer 4 from below. In this process, the screw head 2b is inserted into the cylindrical section 21 while the screw head 2b pressing and expanding the support section 27, which is formed in the lower end of the cylindrical section 21. The space of the notch 23, which is formed in the cylindrical section 21, therefore expands, so that the cylindrical section 21 increases in diameter. When the screw head 2b is accommodated within the washer 4, the space of the notch 23 returns to the original position, and the cylindrical section 21 is restored. The support section 27 moves into the position under the screw head 2b and supports the lower portion of the screw head 2b (see FIG. 10).

Figure 10:
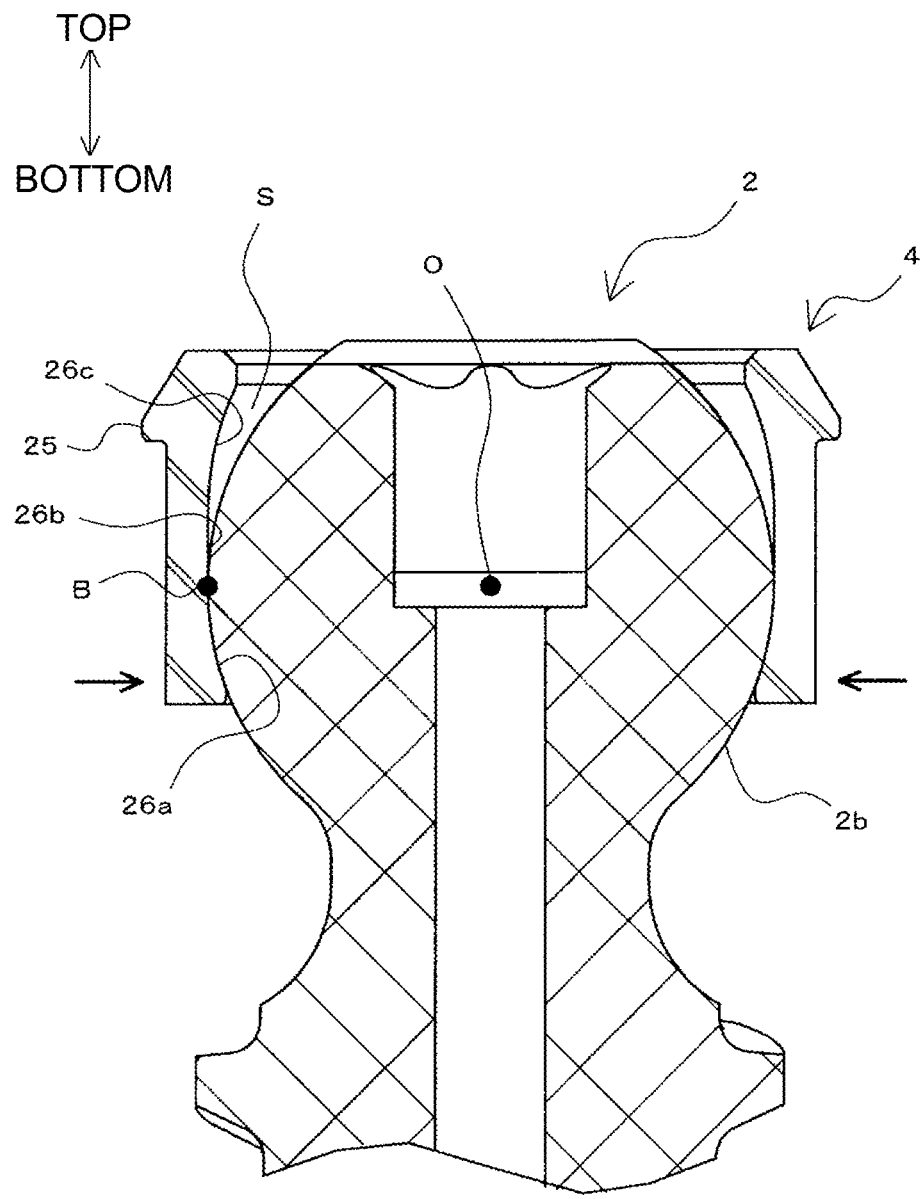
FIG. 10 is a sectional view illustrating a screw head and the washer with the screw head accommodated.

With reference to FIG. 10, the center O of the screw head 2b is located at the substantially same height as the upper end B of the lower concave curve surface 26a, and space S is formed between the upper half of the screw head 2b and the upper concave surface 26c. The space S is thus formed and allows the pawl sections 25 of the washer 4 to bend inside in the process of engaging the pawl sections 25 with the inner circumferential surface of the housing 3 as described later in detail.

With reference to FIG. 10, the inner diameter of the cylindrical inner surface 26b of the washer 4 is smaller than the outer diameter of the screw head 2b as described above. When the screw head 2b is accommodated within the washer 4, the screw head 2b is subjected to a force in such a direction as to tighten the screw head 2b (a radially-inward force, a force in a direction of thick arrows in FIG. 10). This ensures a certain degree of movable resistance of the housing 3 to the screw head 2b. The fixing rod R can be thereby disposed in the housing 3 with the orientation of the housing 3 retained with respect to the screw head 2b to a certain extent. This can improve the handling properties of the spinal implant 1 during the time of surgery.

Next, in step S2, the washer 4 accommodating the screw head 2b therein is engaged within the housing 3. Specifically, the washer 4 accommodating the screw head 2b therein is inserted into the housing 3 from below the housing. In this process, the washer 4 is inserted into the housing 3 with the pawl sections 25, at the upper ends of the segmented sections 22, bent inward by the inner circumferential surface of the housing 3. The pawl sections 25 bend inward since the space S is formed on the back (inside) of the pawl sections 25. When the pawl sections 25 reach the annular groove 14, which is formed in the inner circumferential surface of the housing 3, the segmented sections 22 as the elastic deformable sections are restored, allowing the pawl sections 25 to engage with the annular groove 14. The washer 4 thus engages with the housing 3.

Next, in step S3, the insert 5 is inserted into the housing 3. In this process, the protrusions 36 which are formed in the insert 5, and the respective recesses 16, which are formed in the housing 3 are positioned so as to be aligned in viewing from top-down direction, and then, the insert 5 is inserted into the housing 3, until the protrusions 36 reach the respective recesses 16. The protrusions 36 thus engage with the respective recesses 16, and therefore the insert 5 is fixed in the housing 3. In this state, the lower curved surface 34 of the insert 5 is in contact with the upper part of the screw head 2b. A lower part of the outer circumferential surface of the insert faces an upper part of the inner circumferential surface of the washer 4 with a small gap therebetween or is in contact with the same.

In the spinal implant 1 assembled as described above, the housing 3 and the washer 4 and insert 5 which are accommodated within the housing 3 are rotatable relative to the screw head 2b.

[Procedure to Fix Fixing Rod]

Figure 11:
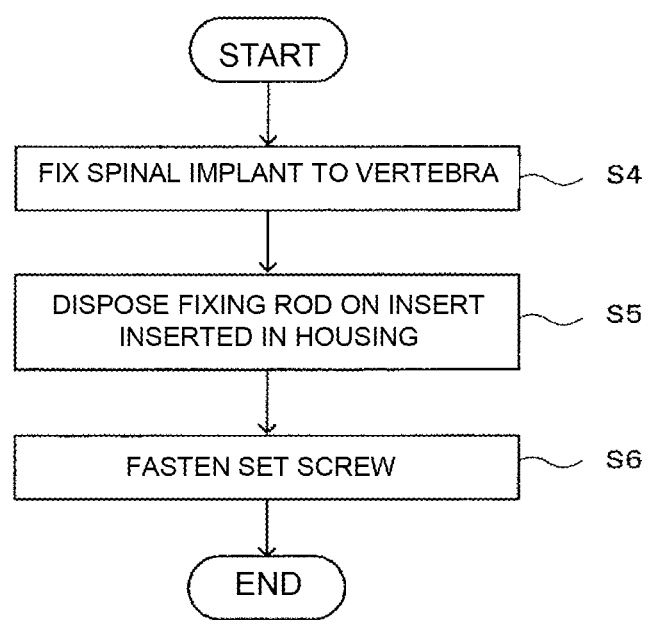
FIG. 11 is a flowchart illustrating the procedure to fix the fixing rod to a patient's vertebra.

FIG. 11 is a flowchart illustrating the procedure to fix the fixing rod R to the vertebrae L of a patient.

First, in step S4, the screw body 2a of the bone screw 2 is screwed and fixed with a driver or the like to each of the vertebrae of the patient who is subjected to spinal fusion.

Next, in step S5, the fixing rod R is disposed on the insert 5 within the housing 3. In this process, the fixing rod R is inserted into the housing 3 and passes through the pair of slits 13, which are formed in the housing 3. The fixing rod R is thereby disposed on the upper concave surface 35 of the insert 5 between the pair of walls 32 of the insert 5.

Eventually, in step S6, the set screw 6 is fastened to the housing 3. In this process, the set screw 6 gradually advances to the position where the set screw 6 presses the fixing rod R downward. The bottom of the set screw 6 comes into contact with the fixing rod R and presses the fixing rod R downward. The screw head 2b is pressed by the set screw 6 with the fixing rod R and insert 5 in between.

Since the bone screw 2 is screwed and fixed to the vertebra L, when the set screw 6 is further fastened in the above-described state, the housing 3 and washer 4 are raised upward relative to the set screw 6, fixing rod R, insert 5, and bone screw 2, between which the relative positional relationship in the top-bottom direction is maintained. In this process, the support section 27 of the washer 4 is caught by the lower part of the screw head 2b, so that the housing 3 is held between the set screw 6 and screw head 2b. This prevents the housing 3 from separating from the screw head 2b while fixing the position and orientation of the fixing rod R with respect to the bone screw 2.

In spinal fusion, the processes of the aforementioned steps S4 to S6 are performed for the spinal implant 1 fixed to each vertebra, so that the vertebrae L are fixed to each other with the fixing rod R.

[Effects]

As described above, in the spinal implant 1 according to the embodiment, the washer 4, housing 3, and insert 5 exert forces on each other to fix the rod R to the bone screw 2 fixed to each vertebra L of a patient. The vertebrae L of the patient are thereby fixed to each other.

Specifically, in the spinal implant 1, the washer 4 holding the screw head 2b is accommodated within the housing 3 and engages with the housing 3. In the spinal implant 1, the insert 5 disposed in the housing 3 is subjected to pressing force by the fixing rod R which is fixed to the housing 3 by the set screw 6 screwed to the housing 3 and presses the screw head 2b downward, so that the housing 3 is fixed to the screw head 2b. The position and orientation of the fixing rod R with respect to the bone screw 2 can be thereby fixed. The aforementioned fixing rod R is fixed as described above and is laid across all of the bone screws 2 fixed to vertebrae L of the patient who is subjected to spinal fusion. The vertebrae L of the patient can be therefore fixed to each other.

In the spinal implant 1, the support section 27 in the cylindrical section 21 of the washer 4 supports the screw head 2b from below. The screw head 2b is prevented by the washer 4 from separating from the housing 3. Additionally, in the spinal implant 1, the cylindrical section 21, which includes the support section 27, is configured to be capable of increasing in diameter. At the assembly of the spinal implant 1, therefore, the screw head 2b is accommodated within the cylindrical section 21 by inserting the screw head 2b into the washer 4 from below.

If a spinal implant is assembled by inserting a bone screw into a washer (or a housing) from above, it is necessary to determine the size of the housing in accordance with the screw diameter of the bone screw, and the housing cannot be used in common. In order to use the housing in common, the housing needs to increase in size.

On the other hand, according to the spinal implant 1, the cylindrical section 21 is elastically deformable (capable of increasing or decreasing in diameter) in the radial direction. This allows for the assembly process in which the screw head 2b can be inserted into the washer 4 from below and the washer 4 holding the screw head 2b is inserted into the housing 3 from below. It is therefore unnecessary to cause the screw body 2a to penetrate the housing 3 at the assembly. The housing 3 reduced in size can be used in common regardless of the screw diameter.

According to the spinal implant 1, the section having the function to hold the screw head 2b in the housing 3 and the section having the function to prevent the screw head 2b from separating from the housing 3 are composed of one member (specifically, the washer 4). This can reduce the number of components compared with when the sections having the aforementioned functions are composed of different components, for example. It is possible to provide the spinal implant that is good at assembling properties.

By disposing the elastic deformable section (the segmented sections 22) which is elastically deformable within the housing 3 to the washer 4 like the spinal implant 1, the washer 4 is smoothly inserted into the housing 3 and easily engages with the housing 3 when the washer 4 holding the screw head 2b is accommodated in the housing 3 in the assembly of the spinal implant. It is therefore possible to provide the spinal implant 1 that is good at assembling properties.

According to the spinal implant 1, it is therefore possible to provide the spinal implant which includes the compact housing 3 usable in common regardless of the diameter of the bone screw 2 and is good at assembling properties.

In the spinal implant 1, the cylindrical section 21 includes the notch 23. This facilitates forming the cylindrical section 21 capable of increasing and decreasing in diameter.

In the spinal implant 1, the plurality of segmented sections 22 constitutes the elastic deformable section. The configuration of the elastic deformable section is thus simplified.

Moreover, in the spinal implant 1, the plurality of segmented sections 22 is disposed above the cylindrical section 21. By disposing the segmented sections 22 to the portion above the cylindrical section which is comparatively less limited in space in the housing 3 as described above, the space in the housing 3 is utilized effectively. This allows the housing 3 to have a reduced size.

By disposing the pawl sections 25, which protrude outward from the top portions of the segmented sections 22, as the engagement section while forming the annular groove 14 configured to engage with the pawl sections 25 in the housing 3, like the spinal implant 1, the shape of the engagement section is thus simplified.

Moreover, in the spinal implant 1, even if the pawl sections 25 are subjected to any radially inward force due to any cause and likely to bend inward, the pawl sections 25 are prevented from bending, by the outer circumferential surface of the insert 5. This can prevent the pawl sections 25 from being disengaged from the annular groove 14 of the housing 3.

In the spinal implant 1, if the screw head 2b is likely to separate from the cylindrical section 21 downward, the outer circumferential surface of the cylindrical section 21 is covered with the inner circumferential surface of the housing 3, and the cylindrical section 21 cannot greatly increase in diameter. This can prevent the screw head 2b from separating from the housing 3.

In the spinal implant 1, the cylindrical inner surface 26b extends upward from the lower concave curve surface 26a, which supports the lower portion of the screw head 2b. The space S is therefore formed between the plurality of segmented sections 22 and screw head 2b in the state where the lower portion of the screw head 2b is supported by the lower concave curve surface 26a. This ensures enough space for the segmented sections 22 to elastically deform, on the back (the screw head 2b side) of the plurality of segmented sections 22 as the elastic deformable section. According to the spinal implant 1, when the washer 4 holding the screw head 2b is inserted into the housing 3 from below, the plurality of segmented sections 22 elastically deforms, allowing the washer 4 to engage with the housing 3 from below.

In the spinal implant 1, the maximum inner diameter D (that is, the inner diameter of the cylindrical inner surface 26b) of the cylindrical section 21 is smaller than the outer diameter of the screw head 2b. When the screw head 2b is accommodated within the cylindrical section 21, the screw head 2b is tightened inward by the cylindrical inner surface 26b of the cylindrical section 21. According to the spinal implant 1, therefore, the screw head 2b is easily retained within the cylindrical section 21.

In the spinal implant 1, the position of the insert 5 in the housing 3 is easily fixed.

In the spinal implant 1, the compact housing 3 can be used in common regardless of the size of the screw diameter. The spinal implant 1 is also good at assembling properties and further includes the bone screw 2.

Hereinabove, the embodiment of the present invention is described. However, the present invention is not limited to the aforementioned embodiment and can be variously changed without departing from the description of claims. The present invention may be modified and implemented as follows, for example.

[Modification]

(1) FIG. 12 illustrates the shape of a washer 4a of a spinal implant according to a modification. FIGS. 12(A) and 12(B) are a plan view and a front view, respectively. The washer 4a of the spinal implant according to the modification is different from the washer 4 of the spinal implant 1 according to the aforementioned embodiment in that the notch 23 is not included but a plurality of slits 28 is included. Hereinafter, the differences between the washer 4a of the modification and the washer 4 of the aforementioned embodiment will be described. Description of the other part is omitted.

The plurality of slits 28 is formed in a cylindrical section 21a of the washer 4a. The slits 28 extend from the lower end of the washer 4a to the middle of the washer 4a in the top-bottom direction. Between slits 28 adjacent in the circumferential direction, segmented sections 29 are formed.

As illustrated in FIG. 12, each slit 28 is disposed between two of the slits 24 adjacent in the circumferential direction. The slits 24 and slits 28 are located alternately in the circumferential direction.

In the process of inserting the screw head 2b into the cylindrical section 21a from below in the assembly of the spinal implant, the segmented sections 29 are pressed and expanded by the screw head 2b to increase the spaces of the slits 28 in the cylindrical section 21a. The cylindrical section 21a thereby increases in diameter as a whole. When the screw head 2b is accommodated within the washer 4, the segmented sections 29 are restored to the original positions. Similarly to the aforementioned embodiment, the support 27 thereby moves into the position under the screw head 2b and supports the screw head 2b from below.

Also by forming the plurality of slits 28 in the cylindrical section 21a like the modification, the cylindrical section can be configured to once increase in diameter when the screw head 2b is inserted from below and then decrease in diameter to be restored. According to the modification, the spinal implant 1 can take a wide variety of shapes.

(2) In the aforementioned embodiment, the cylindrical section takes a C-shape or includes the plurality of slits 28. However, the cylindrical section is not limited thereto. Specifically, the cylindrical section may have any configuration as long as the cylindrical section once increases in diameter and then decreases in diameter to be restored during the process of inserting the screw head 2b from below at the assembly of the spinal implant 1.

(3) In the aforementioned embodiment, the elastic deformable section is composed of the plurality of segmented sections 22. However, the elastic deformable section is not limited thereto. Specifically, the elastic deformable section may take any shape as long as the elastic deformable section can be once elastically deformed and then restored to allow the engagement section to engage with the inner circumferential surface of the housing in the process of inserting the elastic deformable section holding the screw head 2b into the housing 3 from below.

(4) In the aforementioned embodiment, the maximum inner diameter D of the cylindrical section 21 is smaller than the outer diameter of the screw head 2b. However, the cylindrical section is not limited thereto. The cylindrical section may have an inner diameter equal to the outer diameter of the screw head.

(5) In the aforementioned embodiment, the curvature radius of the lower concave curve surface 26a of the cylindrical section 21 is smaller than the radius of the screw head 2b. The cylindrical section is not limited thereto. The curvature radius of the lower concave curve surface 26a may be equal to or greater than the radius of the screw head 2b.

Figure 13:
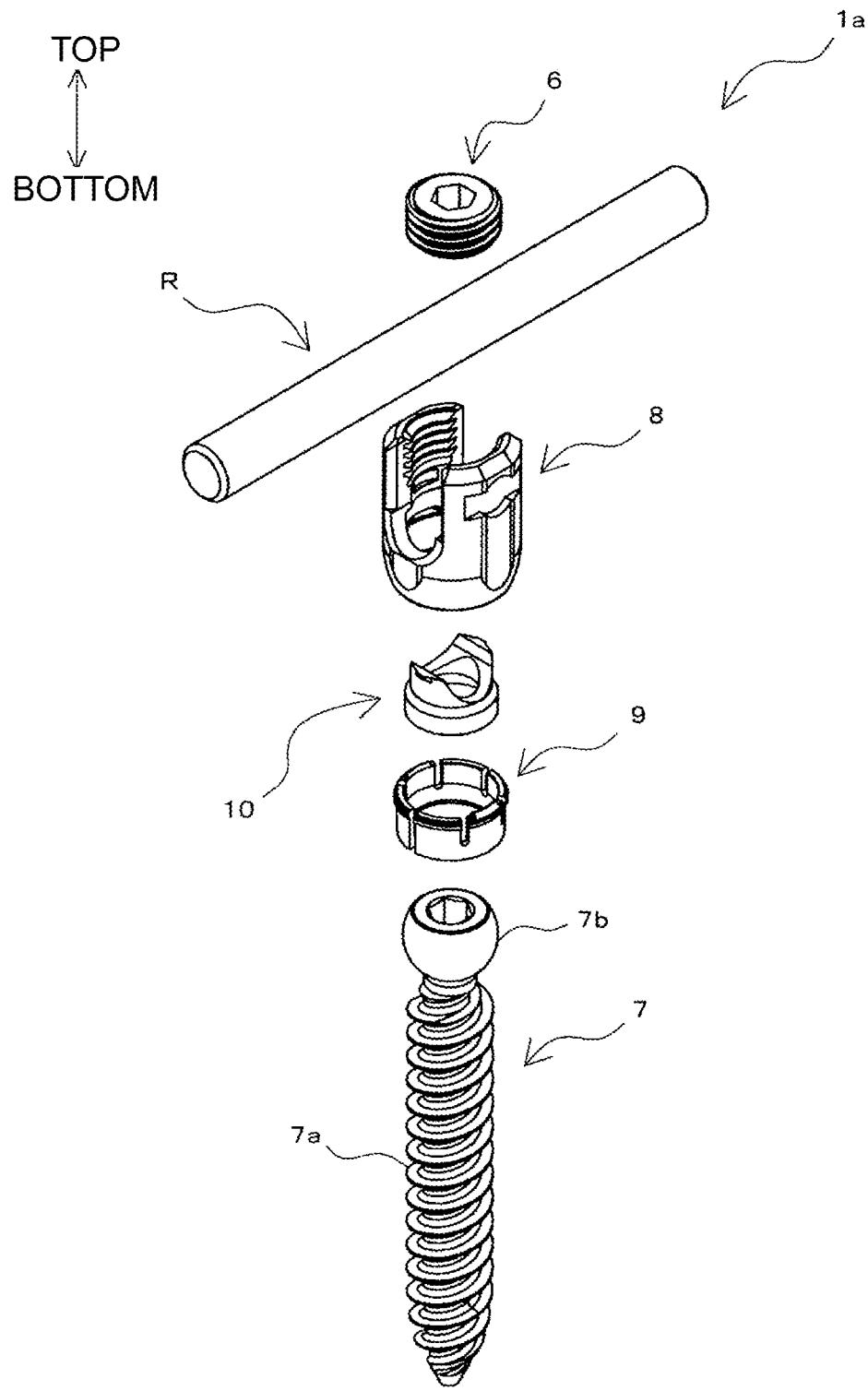
FIG. 13 is an exploded perspective view illustrating the spinal implant according to the modification together with a fixing rod fixed to a vertebra by using the spinal implant.
Figure 14:
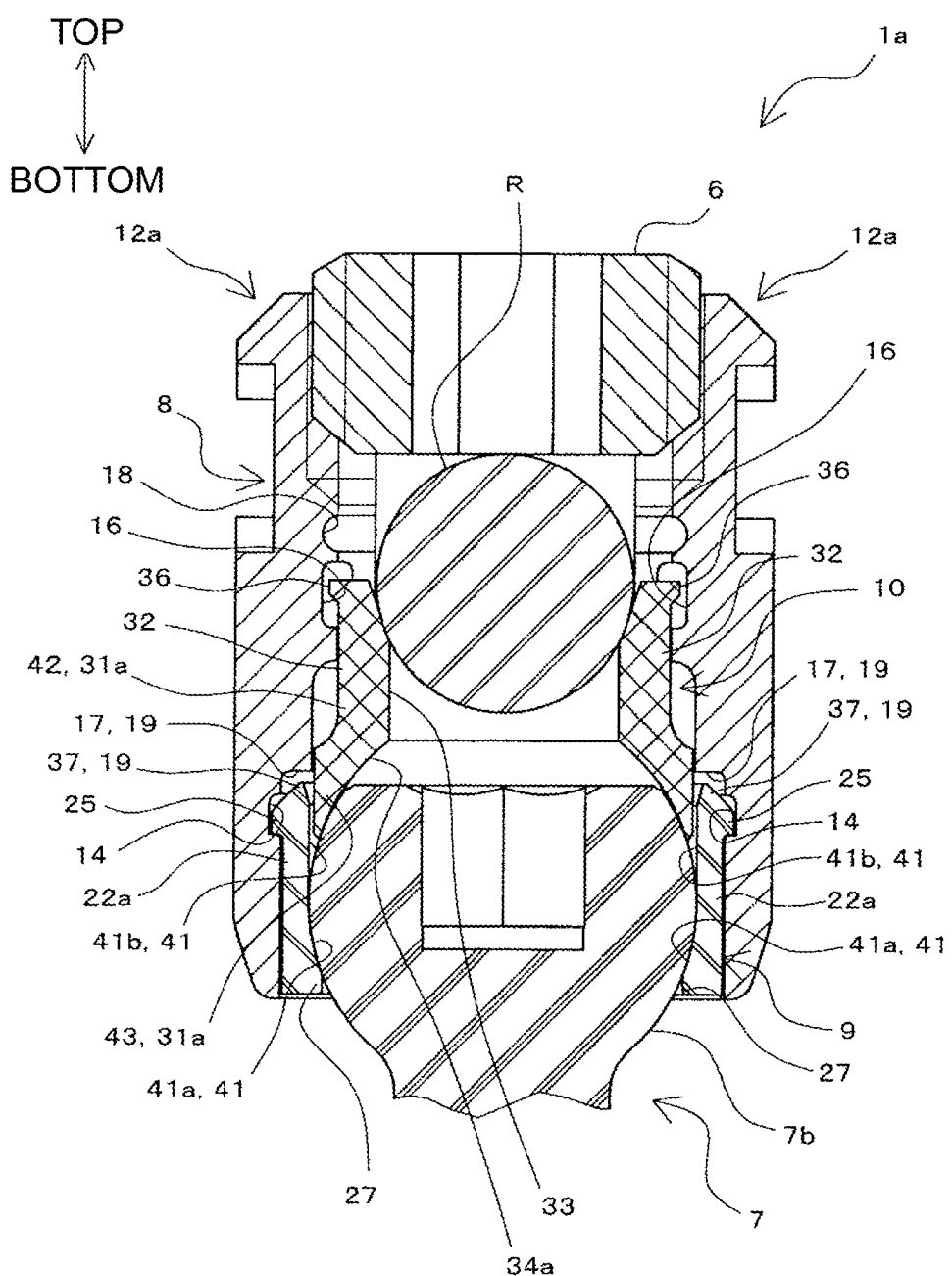
FIG. 14 is a partial longitudinal sectional view of the spinal implant.
Figure 15:
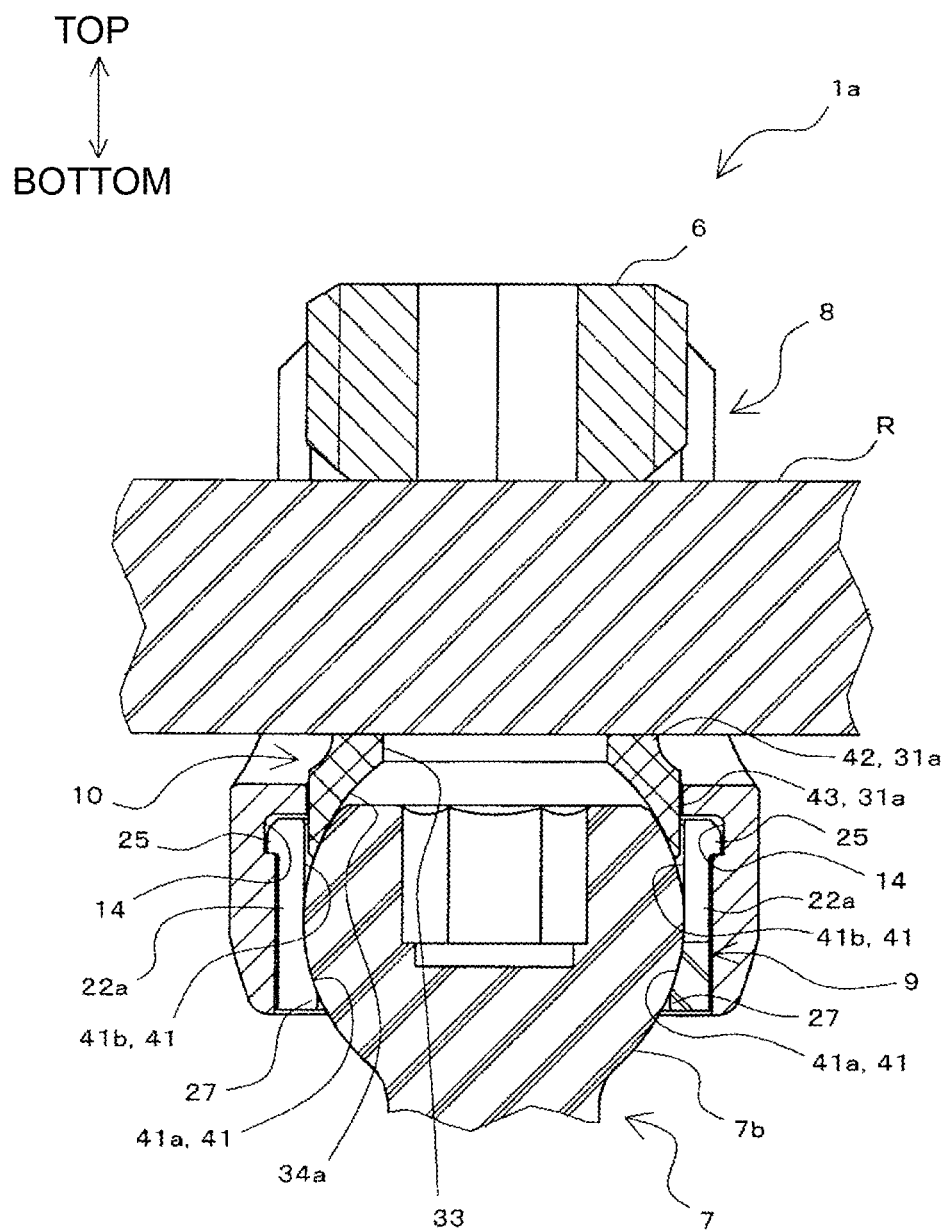
FIG. 15 is a partial longitudinal sectional view of the spinal implant at a different position from that of FIG. 14.

(6) FIG. 13 is an exploded perspective view illustrating a spinal implant 1a according to a modification together with the fixing rod R fixed to the vertebra L by using the spinal implant 1a. FIG. 14 is a partial longitudinal sectional view of the spinal implant 1a. FIG. 15 is a partial longitudinal sectional view of the spinal implant 1a at a position different from that of FIG. 14.

The spinal implant 1a according to the modification is different from the spinal implant 1 according to the aforementioned embodiment in the configurations of the screw, housing, washer, and insert. The following description is mainly given of differences from the aforementioned embodiment, and the other part is not described.

A screw 7 of this modification is different from the screw 2 of the aforementioned embodiment in that the number of ridges of a screw body 7a is different from that of the screw 2 and that the outer diameter of the screw head 7b is larger. The other schematic configuration of the screw 7 is the same as that of the screw 2 of the aforementioned embodiment, and the description thereof is omitted. The usage of the spinal implant 1a according to the embodiment is the same as that of the aforementioned embodiment, and the description thereof is omitted.

A housing 8, a washer (a screw head holding member) 9, and an insert 10, which are used in the spinal implant 1a according to the modification, have configurations particularly suitable for the screw 7 in which the screw head 7b has a larger outer diameter.

[Configuration of Housing]

Figure 16:
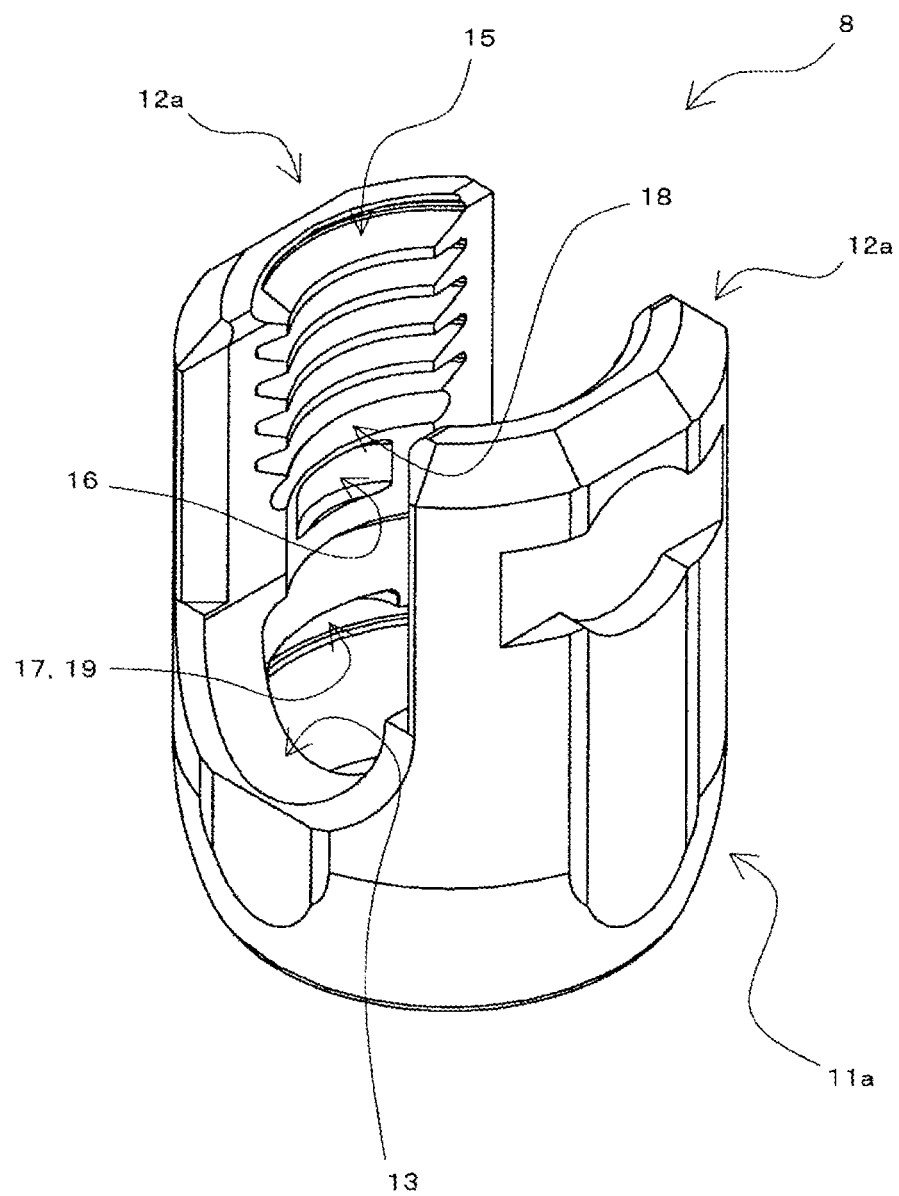
FIG. 16 is a perspective view of a housing.

FIG. 16 is a perspective view of the housing 8. FIG. 17(A) is a longitudinal sectional view of the housing 8. FIG. 17(B) is a longitudinal sectional view of the housing 8 at a different position from that of FIG. 17(A).

Figure 17:
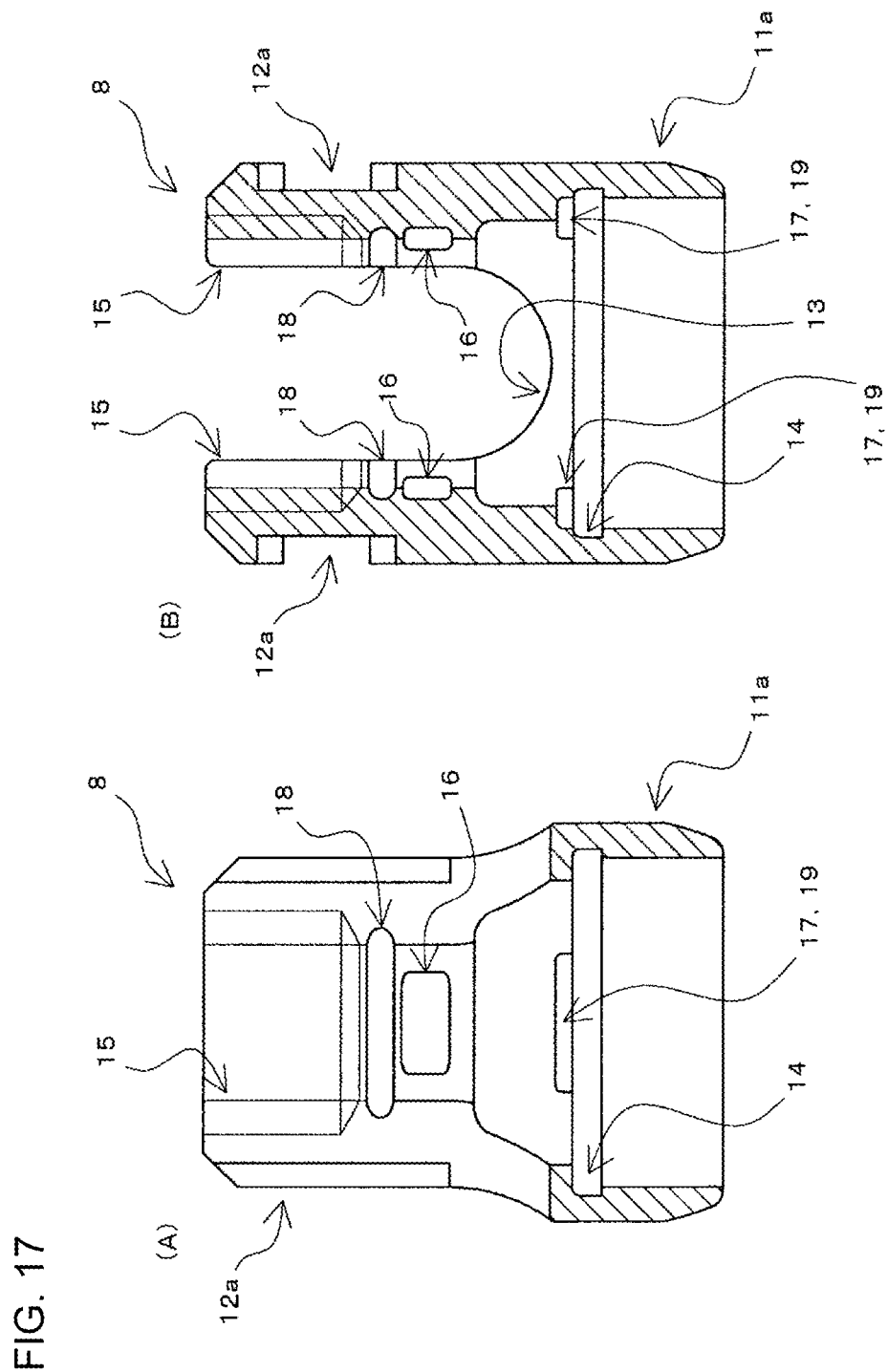
FIG. 17(A) is a longitudinal sectional view of the housing.
FIG. 17(B) is a longitudinal sectional view of the housing at a different position from that of FIG. 17(A).

With reference to FIG. 16 and FIG. 17, the housing 8 includes a base 11a and a pair of tabs 12a, which are formed integrally. The base 11a is a substantially cylindrical section, and the tabs 12a extend upward from the base 11a. Between the pair of tabs 12, the pair of slits 13, to which the fixing rod R is disposed, is formed. The configurations of the base 11a and tabs 12a are different from those of the aforementioned embodiment to some extent.

Similarly to the base 11 of the aforementioned embodiment, the base 11a includes the annular groove 14 extending in a portion of the inner circumferential surface of the base 11a on the tabs 12 side. The annular groove 14 is engaged with the pawl sections 25 of the washer 4 described later in detail.

In the inner side of the base 11a, two recesses 17 and 17 are formed. The recesses 17 are disposed under the respective tabs 12a and are depressed upward from the annular groove 14 with reference to FIG. 16 and FIG. 17. The recesses 17 constitute housing rotation restricting mechanisms 19 in conjunction with protrusions 37 of a washer 9 described in detail later. The housing rotation restricting mechanisms 19 limit rotation of the housing 8 relative to the washer 9.

In upper part of the inner side surface of each tab 12, the internal thread 15, which is screwed to the set screw 6, is formed in a similar manner to the aforementioned embodiment. FIGS. 14, 15, 17(A), and 17(B) illustrate the internal thread 15 schematically.

In a similar manner to the aforementioned embodiment, each recess 16 is formed in the portion of the inner circumferential surface of the corresponding tab 12 which is a little below the internal thread 15. The recesses 16 are configured to engage with the protrusions 36 of the insert 10.

In each tab 12, a rotation allowing groove 18 is formed. The rotation allowing groove 18 is an arc-shaped groove disposed between the internal thread 15 and recess 16 in the top-bottom direction. In the spinal implant 1a according to the modification, to be described in detail later, the rotation allowing groove 18 facilitates the assembling work in the process of assembling the insert 10 to the housing 8.

[Configuration of Washer]

Figure 18:
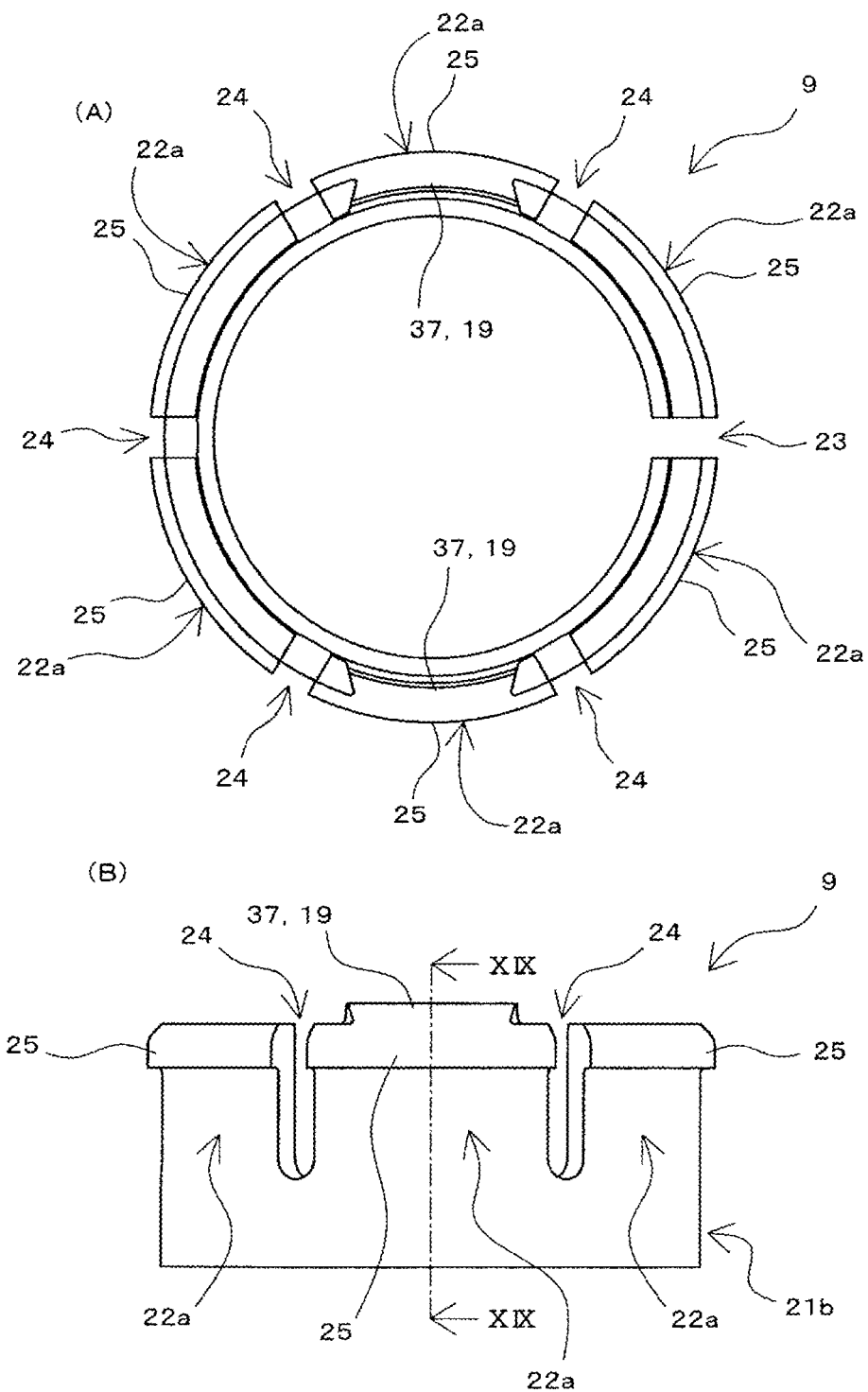
FIGS. 18(A) and 18(B) illustrate the shape of the washer, FIGS. 18(A) and 18(B) being a plan view and a front view, respectively.
Figure 19:
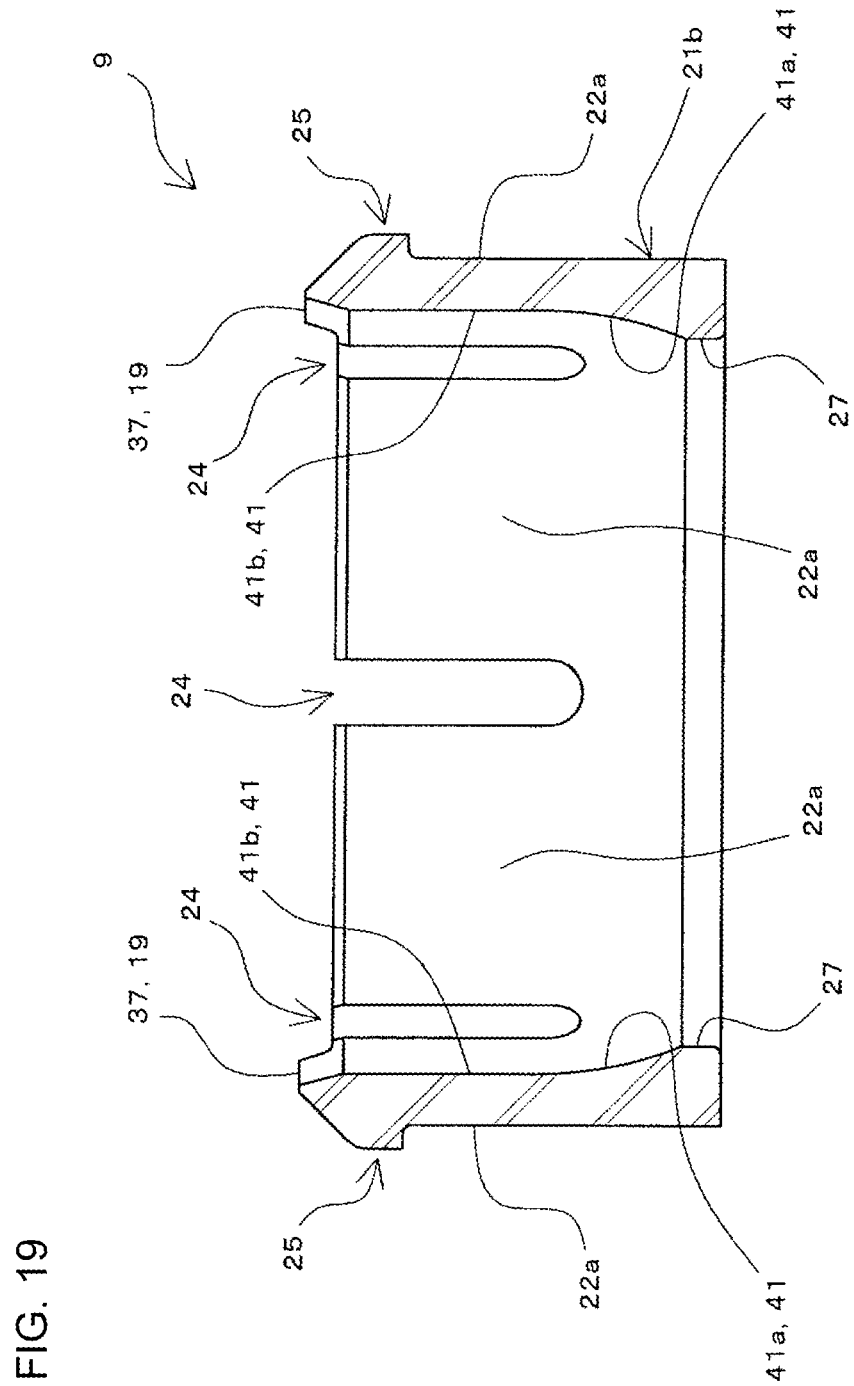
FIG. 19 is an enlarged sectional view along a line XIX-XIX of FIG. 18(B).

FIG. 18 illustrates the shape of the washer 9. FIGS. 18(A) and 18(B) are a plan view and a front view, respectively. FIG. 19 is an enlarged sectional view along a line XIX-XIX of FIG. 18(B).

The washer 9 of the modification includes a cylindrical section 21b and a plurality of segmented sections 22a, which are formed integrally. The washer 9 of the modification and the washer 4 of the embodiment have mainly three differences in structure as follows. The first difference is that the cylindrical section 21b has the maximum inner diameter a little greater than that of the washer 4 and holds the screw head 7b, which has a diameter greater than the screw head 2b of the bone screw 2 of the aforementioned embodiment. The second difference is the difference in the shape of the inner circumferential surface. The third difference is that some of the segmented sections 22a include the protrusions 37. Hereinafter, the aforementioned second and third differences are mainly described, and description of the other part is omitted.

In the example of the washer 4 of the aforementioned embodiment described with reference to FIG. 7, the inner circumferential surface 26 of the washer 4 is composed of the lower concave curve surface 26a, cylindrical inner surface 26b, and upper concave surface 26c. In this respect, an inner circumferential surface 41 of the washer 9 of the modification includes a lower concave curve surface 41a and a cylindrical inner surface 41b as illustrated in FIG. 19.

The lower concave curve surface 41a is a part of a spherical concave surface and is disposed as the lower half of the inner circumferential surface 41 of the washer 9. The lower concave curve surface 41a supports the lower portion of the screw head 7b. The curvature radius of the lower concave curve surface 41a is smaller than the curvature radius of the screw head.

The cylindrical inner surface 41b is disposed as the upper half of the inner circumferential surface 41 of the washer and extends upward from the upper end of the lower concave curve surface 41a. The cylindrical inner surface 41b has a straight line profile extending in the top-bottom direction when viewed in a direction perpendicular to the top-bottom direction. The cylindrical inner surface 41b is disposed as the maximum inner diameter section having the largest inner diameter in the inner circumferential surface 41 of the washer 9. The radius of the cylindrical inner surface 41b is the same as the curvature radius of the lower concave curve surface 41a. The inner diameter of the cylindrical inner surface 41b is smaller than the outer diameter of the screw head 7b.

The protrusions 37 protrude upward from the respective tops (upper ends) of the segmented sections 22a. In the modification, two protrusions 37 are disposed. Specifically, with reference to FIG. 18(A), when the segmented section next to the notch 23 in the clockwise direction is set as a first segmented section, the protrusions 37 are disposed in second and fifth segmented sections. Each protrusion 37 has a substantially arc shape extending in the circumferential direction when viewed in the top-bottom direction. As described above, the protrusions 37 constitute the housing rotation restricting mechanisms 19 in conjunction with the recesses 17, which are formed in the housing 8.

[Configuration of Housing Rotation Restricting Mechanism]

The housing rotation restricting mechanisms 19 include the recesses 17 of the housing 8 and the protrusions 37 of the washer 9 as described above. With reference to FIGS. 14, 16, and (mainly FIG. 14), in the housing rotation restricting mechanisms 19, each recess 17 covers a top portion of the corresponding protrusion 37 from above. Even if the housing 8 is likely to rotate relative to the washer 9, the recesses 17 are caught by the protrusions 37 and cannot rotate, and thus rotation of the housing 8 relative to the washer 9 is restricted.

[Configuration of Insert]

Figure 20:
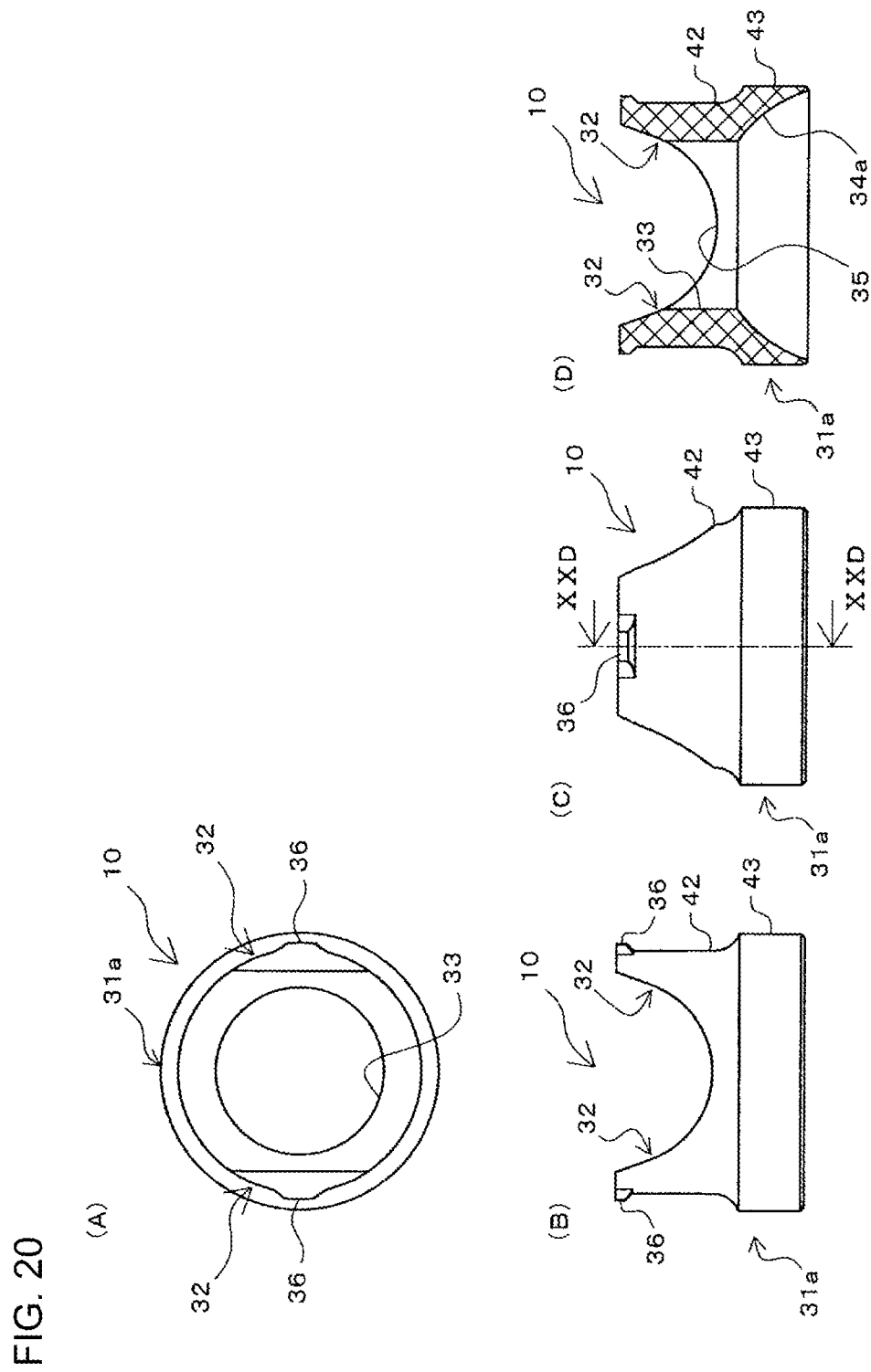
FIGS. 20(A) to 20(D) illustrate the shape of an insert, FIGS. 20(A) to 20(D) being a plan view, a front view, a side view, and a sectional view along a line XXD-XXD of FIG. 20(C), respectively.

FIG. 20 illustrates the shape of the insert 10. FIGS. 20(A) to 20(D) are a plan view, a front view, a side view, and a sectional view along a line XXD-XXD of FIG. 20(C), respectively.

The insert 10 of the modification is significantly different from the insert 5 of the aforementioned embodiment in the base configuration. Hereinafter, the configuration of a base 31a in the insert 10 of the modification is described, and description of the configuration of the other part is omitted.

The base 31a of the modification includes an upper base 42 and a lower base 43, which are formed integrally.

The upper base 42 is the upper half of the base 31a. The upper base 42 is a cylindrical section thinner in the top-bottom direction. Within the upper base 42, a through-hole 33 extends in the top-bottom direction.

The lower base 43 is the lower half of the base 31a. The lower base 43 is a substantially cylindrical section extending in the top-bottom direction. The outer diameter of the lower base 43 is greater than the outer diameter of the upper base 42. The outer diameter of the lower base 43 is also greater than the outer diameter of the base 31 of the aforementioned embodiment. The outer circumferential surface of the lower base 43 connects to the outer circumferential surface of the upper base 42 in a rounded manner.

In lower part of the lower base 43, a lower curved section 34a having a curved surface is formed. The lower curved section 34a has a shape that allows upper part of the screw head 7b to substantially fit to the lower curved section 34a without a gap. The curvature radius of the lower curved section 34a is greater than the curvature radius of the lower curved section 34 of the aforementioned embodiment. The area of contact between the lower curved section 34a and screw head 7b is larger than that between the lower curved section 34 and screw head 2b in the aforementioned embodiment.

[Assembly Process of Spinal Implant]

Figure 21:
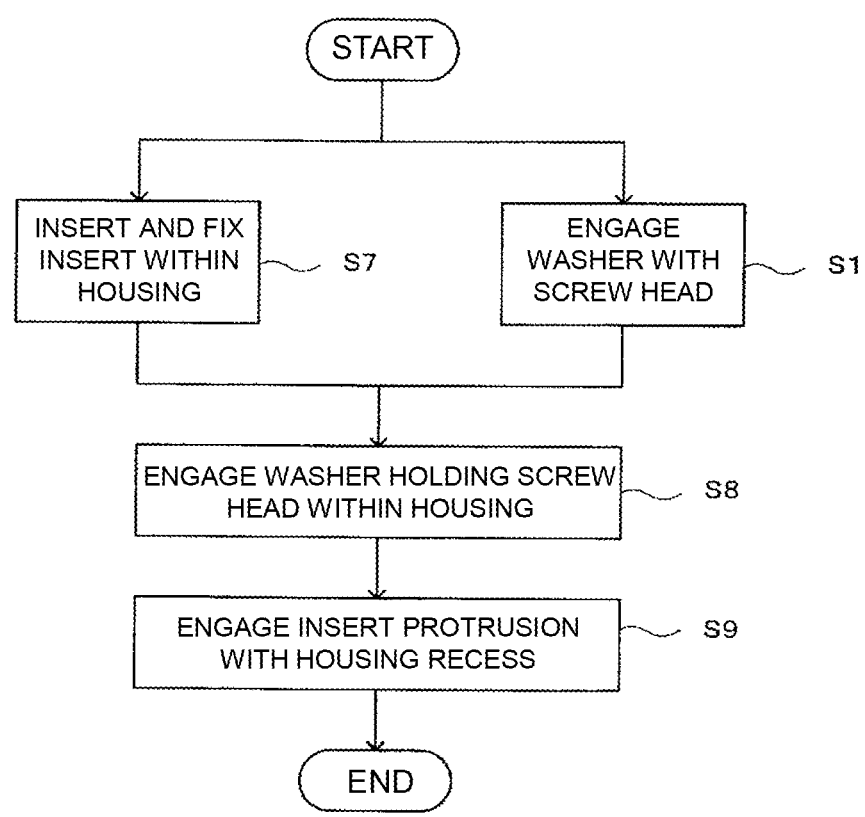
FIG. 21 is a flowchart illustrating an assembly process of the spinal implant.
Figure 22:
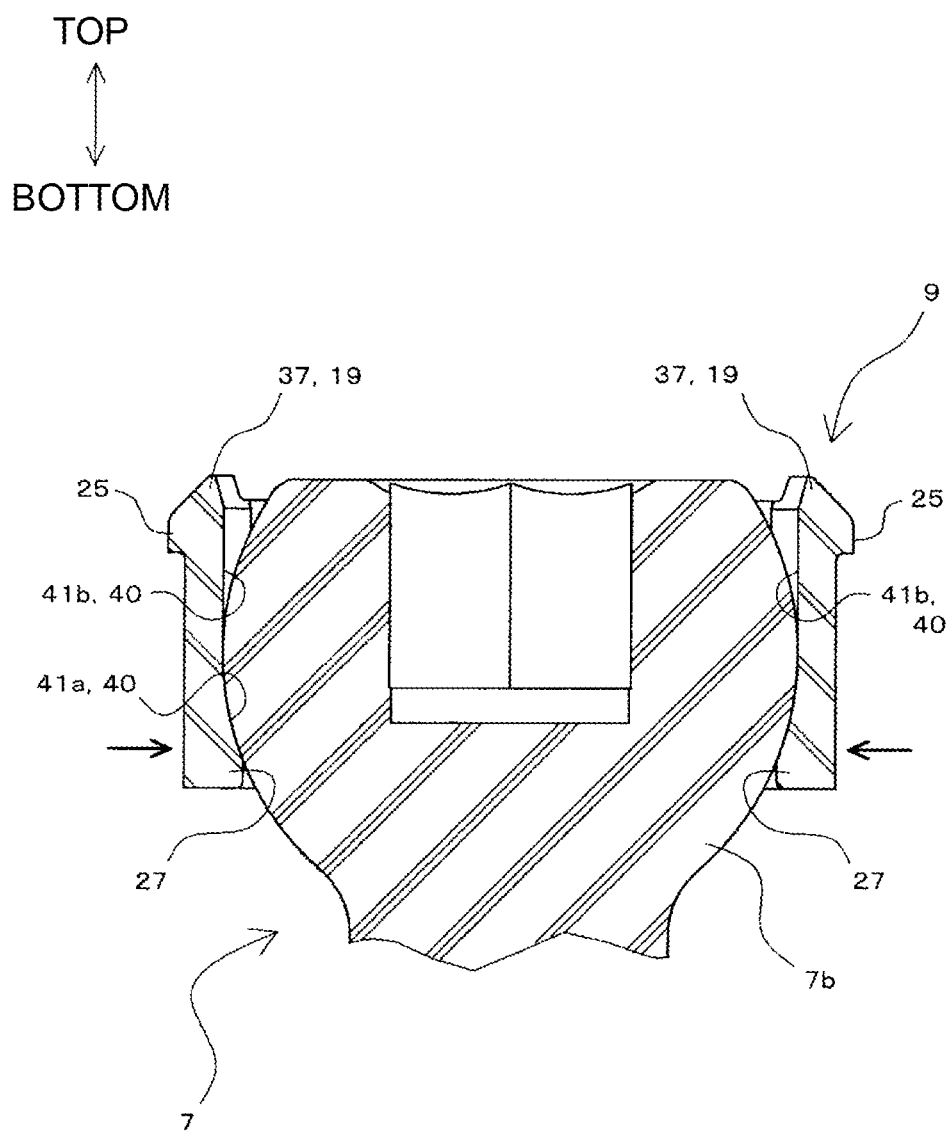
FIG. 22 is a sectional view of the screw head and the washer holding the screw head.

FIG. 21 is a flowchart illustrating the assembly process of the spinal implant 1a. FIG. 22 is a sectional view of the screw head 7b and the washer 9 holding the screw head 7b.

Figure 23:
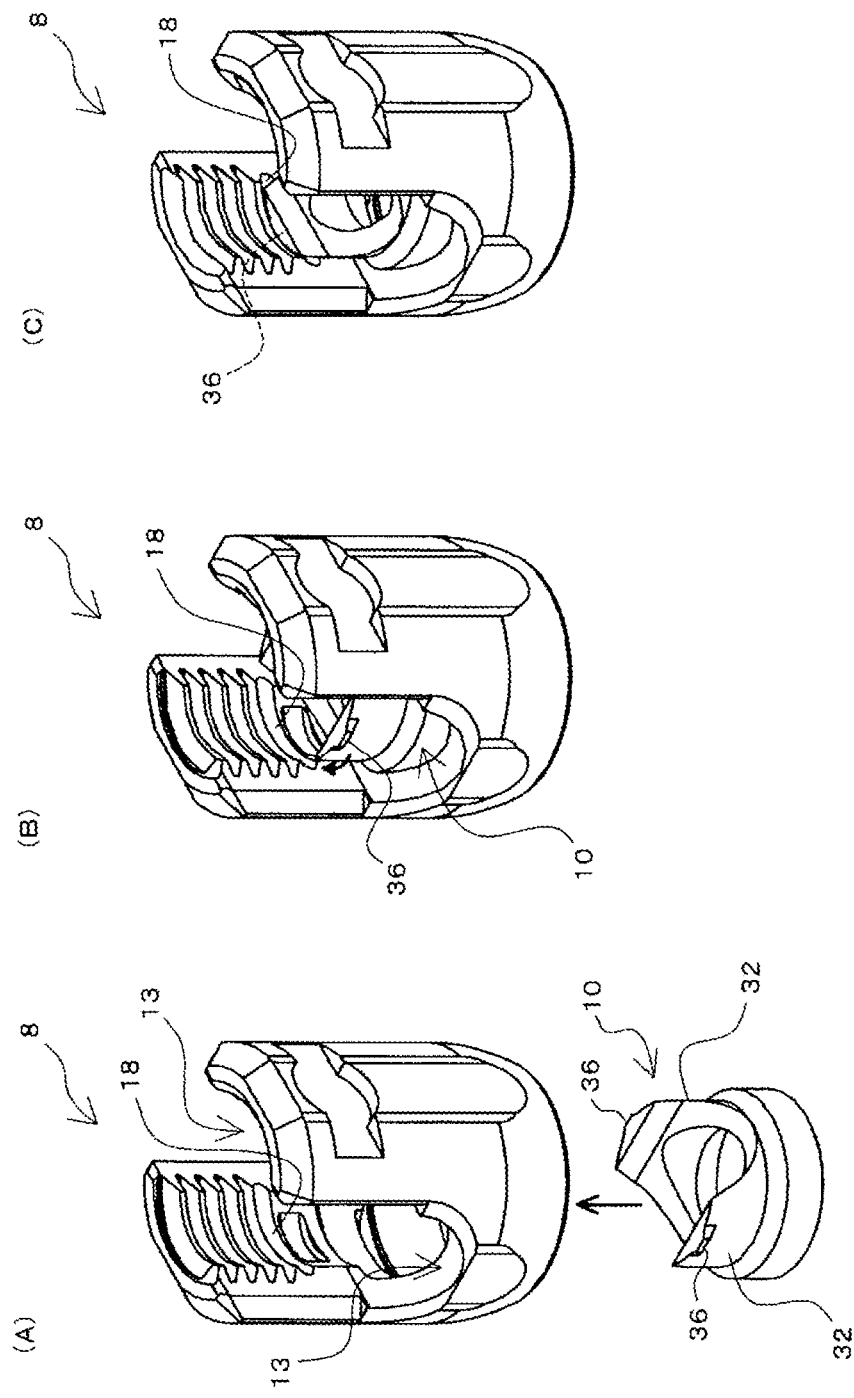
FIGS. 23(A) to 23(C) are illustrations for describing the process performed in step S7 in FIG. 21, FIG. 23(A) illustrating the state of the insert before the insert is inserted into the housing.

FIGS. 23(A) to 23(C) are illustrations for describing the process performed in step S7 of FIG. 21. FIG. 23(A) illustrates the state of the insert 10 before the insert 10 is inserted into the housing 8. FIG. 23(B) illustrates the state of the insert 10 inserted in the housing 8. FIG. 23(C) illustrates the insert 10 rotated within the housing 8. FIGS. 24(A) to 24(C) illustrate the process performed in the steps S8 and S9 of FIG. 21. FIG. 24(A) illustrates the state of the screw head 7b and washer 9 before the screw head 7b and washer 9 are inserted into the housing 8. FIG. 24(B) illustrates the state of the screw head 7b and washer 9 inserted in the housing 8. FIG. 24(C) illustrates the state where the protrusions 36 of the insert 10 engage with the recesses 16 of the housing 8. Hereinafter, the assembly process of the spinal implant 1a is described with reference to FIGS. 21 to 24.

First, in the step S1, the washer 9 is engaged with the screw head 7b (see FIG. 22). Specifically, in the same manner as the aforementioned embodiment, the screw head 7b is inserted upward into the washer 9 from below the washer 9. In this process, the support section 27 moves into the position under the screw head 7b and supports the screw head 7b from below.

In this state, with reference to FIG. 22, space is formed between the upper half of the screw head 7b and upper part of the cylindrical inner surface 41b. Formation of such space allows the pawl sections 25 of the washer 9 to bend inward in the process of engaging the pawl sections 25 with the inner circumferential surface of the housing 8.

With reference to FIG. 22, the inner diameter of the cylindrical inner surface 41b of the washer 9 is smaller than the outer diameter of the screw head 7b as described above. When the screw head 7b is accommodated within the washer 9, the screw head 7b is subjected to a force in such a direction as to tighten the screw head 7b (a radially-inward force, a force in a direction of thick arrows in FIG. 22). This ensures a certain degree of movable resistance of the housing 8 to the screw head 7b. The fixing rod R can be disposed in the housing 8 with the orientation of the housing 8 held with respect to the screw head 7b to a certain extent. This can improve the handling properties of the spinal implant 1a during the time of surgery.

On the other hand, before or after the step S1 or in parallel to the step S1, the insert 10 is inserted and fixed in the housing 8 in the step S7.

Specifically, first in the step S7, with reference to FIG. 23, the insert 10 is inserted into the housing 8 with the walls 32 of the insert 10 aligned with the respective slits 13 of the housing 8 in the circumferential direction (see FIG. 23(A)). The insert 10 is thus accommodated within the housing 8 (see FIG. 23(B)). The protrusions 36, which are disposed in the insert 10, are located at the same position in the top-bottom direction as that of the rotation allowing groove 18 disposed in the housing 8.

In the step S7, the insert 10 in the state illustrated in FIG. 23(B) is rotated by about 90 degrees within the housing 8. The protrusions 36 of the insert 10 then move along the rotation allowing groove 18 of the housing 8. The protrusions 36 are therefore caught by the rotation allowing groove 18. The insert 10 cannot separate downward from the housing 8 and can be fixed within the housing 8 (see FIG. 23(C)).

After the aforementioned steps S1 and S7, step S8 is performed.

In the step S8, the washer 9 holding the screw head 7b is engaged within the housing 8. Specifically, with reference to FIGS. 24(A) to 24(D), the washer 9 holding the screw head 7b is moved into the housing 8 from below the housing 8 in the step S8 (see FIG. 24(A)). In this process, the washer 9 is inserted into the housing 8 with the protrusions 37 of the washer 9 aligned with the recesses 17 of the housing 8 in the circumferential direction. The washer 9 moves upward in the housing 8 while the pawl sections 25 of the washer 9 bend inward due to the lower inner surface of the housing 8. When the pawl sections 25 reach the annular groove 14, the segmented sections 22a as the elastic deformable sections are restored, allowing the pawl sections 25 to engage with the annular groove 14 (see FIG. 24(B)). The washer 9 is thus engaged with the housing 8. The protrusions 37 of the washer 9 are covered with the respective recesses 17 of the housing 8 from above (see FIG. 24(B)).

Next, in the step S9, the protrusions 36 of the insert 10 are engaged with the recesses 16 of the housing 8. Specifically, the insert 10 is pressed downward (in the direction of a thick arrow of FIG. 24(B)). The walls 32 of the insert 10 bend inward slightly as the protrusions 36 of the insert 10 move over the wall between the rotation allowing groove 18 and recesses 16, and the protrusions 36 reach the recesses 16. The protrusions 36 of the insert 10 thus engage with the recesses 16 of the housing (see FIG. 24(C)). As illustrated in FIG. 24(C), the lower curved section 34a of the insert 10 is in tight contact with the screw head 7b.

The spinal implant 1a is assembled by the steps described above. The assembly procedure of the spinal implant 1a is not limited to the aforementioned procedure. For example, after the insert 10 is inserted into the housing 8 in the step S7 (see FIG. 23(B)), the washer 9 holding the screw head 7b may be engaged within the housing 8 before the insert 10 is rotated within the housing 8. The procedure to fix the fixing rod R to the vertebrae L of the patient is the same as that of the aforementioned embodiment, and the description thereof is omitted.

[Advantages]

As described above, according to the spinal implant 1a according to the modification, similarly to the aforementioned embodiment, it is possible to provide a spinal implant which includes the compact housing 8 usable in common regardless of the diameter of the bone screw 7 and which is good at assembling properties.

In the spinal implant 1a, the housing rotation restricting mechanisms 19 limit rotation of the housing 8 relative to the washer 9. This can prevent the housing 8 from rotating and changing the orientation under the own weight or by any external force after the bone screw 7 is embedded in the patient's bone and the housing 8 is sets to a predetermined orientation with respect to the bone screw 7 during the time of surgery. According to the spinal implant 1a, the spinal implant can be held at a predetermined orientation after being fixed to a bone, and the spinal implant with good handling properties is provided.

In the spinal implant 1a, the housing rotation restricting mechanisms 19 are composed of the protrusions 37 and recesses 17, which are elements having comparatively simplified shapes. According to the spinal implant 1a, each housing rotation restricting mechanism 19 is implemented in a simplified form.

In the example described in the modification, the housing rotation restricting mechanisms 19 are composed of the recesses in the housing 8 and the protrusions 37 in the washer 9. However, the housing rotation restricting mechanisms are not limited thereto. The housing rotation restricting mechanisms may have any configuration as long as the mechanisms are capable of restricting rotation of the housing to the washer. For example, with reference to FIG. 14, the housing rotation restricting mechanisms may be composed of protrusions protruding downward from portions of the housing 8 where the recesses 17 are disposed and recesses depressed downward from the portions of the washer 9 where the protrusions 37 are disposed. Alternatively, with reference to FIG. 18, the slits 24 of the washer 9 may be used as recesses. With this, the housing rotation restricting mechanisms can be implemented by forming protrusions protruding downward from portions of the housing 8 where the recesses are disposed.

In the spinal implant 1*a*, the lower base 43 of the insert 10 can be comparatively large. The area of contact between the insert 10 and screw head 7*b* is accordingly large. When the rod R is fixed by the set screw 6 screwed to the housing 8, the insert comes into tight contact with the screw head 7*b* through a wider area, so that the force to fix the housing 8 to the bone screw 7 is increased.

IF the inner space surrounded by the portions of the segmented sections of the washer, where the pawl sections are disposed, narrows with the height unlike the modification, for example, the lower base of the insert disposed within the segmented sections is limited in size.

In this respect, in the spinal implant 1*a*, the inner space surrounded by the portions of the segmented sections 22*a* where the pawl sections 25 are disposed does not narrow and forms a cylindrical shape extending in the top-bottom direction. Even if the outer diameter of the lower base 43 of the insert 10 is increased, therefore, the lower base 43 does not interfere with the washer 9. According to the spinal implant 1*a*, the washer 9 is suitable for the insert 10 in which the lower base 43 has a larger diameter.

According to the spinal implant 1*a*, in the spinal implant 1*a* including the assembly process of inserting the insert 10 into the housing 8 from below, the assembling work of the insert 10 to the housing 8 is facilitated. Specifically, in the process of inserting the insert 10 into the housing 8 from below, the protrusions 36 of the insert 10 are inserted to the same height as the rotation allowing groove 18, then rotated to the positions above the respective recesses 16 of the housing 8, and then pressed downward to engage with the recesses 16. According to the spinal implant 1*a*, it is possible to provide a spinal implant good at assembling properties.

According to the spinal implant 1*a*, the insert 10 and the washer 9 holding the screw head 7*b* can be inserted into the housing 8 from below. According to the spinal implant 1*a*, all the components within the housing 8 can be inserted in the same direction. This can provide a spinal implant good at assembling properties.

INDUSTRIAL APPLICABILITY

The present invention is widely applicable to spinal implants to hold a fixing rod that fixes vertebrae to each other.

REFERENCE SIGNS LIST

1, 1*a* SPINAL IMPLANT
2, 7 BONE SCREW
2*a*, 7*a* SCREW BODY
2*b*, 7*b* SCREW HEAD
3, 8 HOUSING
4, 4*a*, 9 WASHER (SCREW HEAD HOLDING MEMBER)
5, 10 INSERT
6 SET SCREW
21, 21*a*, 21*b* CYLINDRICAL SECTION
22, 22*a* SEGMENTED SECTION (ELASTIC DEFORMABLE SECTION)
25 PAWL SECTION (ENGAGEMENT SECTION)
27 SUPPORT SECTION
L VERTEBRA
R FIXING ROD (ROD)

The invention claimed is:

1. A spinal implant that fixes a rod to a vertebra, the spinal implant comprising:
a bone screw that is configured to be fixed to the vertebra, wherein the bone screw includes:
a screw head,
a screw body that is adapted to be screwed to the vertebra, and
an external thread on an outer circumference of the screw body;
a screw head holding member that holds the screw head of the bone screw via an outer surface of the screw head, wherein the screw head holding member includes:
a cylindrical section that is elastically deformable in a radial direction and includes a support section that supports the screw head from a lower side, wherein the lower side denotes a side to which the screw body extends from the screw head,
an engagement section, and
an elastic deformable section that is elastically deformable in the radial direction of the cylindrical section;
a housing that accommodates the screw head holding member and holds the rod, wherein the housing includes a groove in along an inner circumference of the housing;
an insert that is disposed on top of the screw head within the housing and fixes the housing to the screw head,
wherein the insert includes a protrusion that engages the groove when the insert is inserted in the housing using a first force,
wherein the groove allows the insert to rotate within the housing,
wherein the elastic deformable section comprises a first set of slits extending from a lower end of the cylindrical section to a position below an upper end of the cylindrical section and second set of slits extending from an upper end of the elastic deformable section to a position below a lower end of the elastic deformable section,
wherein the screw head holding member further comprises a plurality of segmented sections each of which extends from the cylindrical section in an axial direction of the cylindrical section and comprises the engagement section at a top portion of each of the segmented sections,
wherein the plurality of segmented sections serves as the elastic deformable section,
wherein the engagement section comprises a pawl section protruding outward from the top portion of a corresponding segmented section, and
wherein the housing comprises a groove that engages with the pawl section.

2. The spinal implant according to claim 1, wherein the plurality of segmented sections extends upward from the cylindrical section.

3. The spinal implant according to claim 1, wherein an outer circumferential surface of the insert is located inside of a portion, where the pawl section is disposed on the segmented section.

4. The spinal implant according to claim 3, wherein
a lower section of the insert serves as a lower base having an outer diameter greater than an outer diameter of an upper base which is a section of the insert above the lower base, and
an outer circumferential surface of the lower base is located inside of the portion, where the pawl section is disposed on the segmented section.

5. The spinal implant according to claim 4, wherein
an inner space surrounded by the top portions of the plurality of segmented sections where the pawl sections are disposed has a cylindrical shape extending in a top-bottom direction.

6. The spinal implant according to claim 1, wherein
an inner circumferential surface of the housing surrounds an outer circumferential surface of the cylindrical section.

7. The spinal implant according to claim 1, wherein
an inner circumferential surface of the cylindrical section comprises:
a lower concave curve surface that is disposed as a lower section of the inner circumferential surface and supports a lower portion of the screw head; and
a cylindrical inner surface extending upward from the lower concave curve surface.

8. The spinal implant according to claim 7, wherein
an inner diameter of the cylindrical inner surface is smaller than an outer diameter of the screw head.

9. The spinal implant according to claim 1, wherein the first set of slits and the second set of slits are located alternately in the circumferential direction.

10. A spinal implant that fixes a rod to a vertebra, the spinal implant comprising:
a bone screw that is configured to be fixed to the vertebra, wherein the bone screw includes:
a screw head,
a screw body that is adapted to be screwed to the vertebra, and
an external thread on an outer circumference of the screw body;
a screw head holding member that holds the screw head of the bone screw via an outer surface of the screw head, wherein the screw head holding member includes:
a cylindrical section that is elastically deformable in a radial direction and includes a support section that supports the screw head from a lower side, wherein the lower side denotes a side to which the screw body extends from the screw head,
an engagement section, and
an elastic deformable section that is elastically deformable in the radial direction of the cylindrical section;
a housing that accommodates the screw head holding member and holds the rod, wherein the housing includes a groove in along an inner circumference of the housing;
an insert that is disposed on top of the screw head within the housing and fixes the housing to the screw head wherein the insert includes a protrusion that engages the groove when the insert is inserted in the housing using a first force,
wherein the groove allows the insert to rotate within the housing,
wherein the housing further includes recesses that are located closer to the screw head than the groove on the inner circumference of the housing,
wherein the protrusion engages the recesses when the protrusion is aligned with the recess and a second force is subsequently applied, and
wherein the recess prohibits rotation about the housing.

* * * * *